(12) United States Patent
Kroll

(10) Patent No.: US 6,745,073 B1
(45) Date of Patent: Jun. 1, 2004

(54) SYSTEM AND METHOD OF GENERATING A LOW-PAIN MULTI-STEP DEFIBRILLATION WAVEFORM FOR USE IN AN IMPLANTABLE CARDIOVERTER/ DEFIBRILLATOR (ICD)

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 339 days.

(21) Appl. No.: 09/967,647

(22) Filed: Sep. 28, 2001

Related U.S. Application Data

(63) Continuation-in-part of application No. 09/803,271, filed on Mar. 9, 2001, now Pat. No. 6,484,056, which is a continuation-in-part of application No. 09/073,394, filed on May 5, 1998, now Pat. No. 6,233,483.

(60) Provisional application No. 60/046,610, filed on May 15, 1997.

(51) Int. Cl.[7] ............................... A61N 1/39

(52) U.S. Cl. ............................... 607/7; 607/5

(58) Field of Search ............................... 607/5, 63, 46, 607/7, 72, 74, 68

(56) References Cited

U.S. PATENT DOCUMENTS

| | | | |
|---|---|---|---|
| 4,768,512 A | 9/1988 | Imran ..................... | 128/419 D |
| 4,850,357 A | 7/1989 | Bach, Jr. ................ | 128/419 D |
| 5,083,562 A | 1/1992 | De Coriolis et al. .... | 128/419 D |
| 5,184,616 A | 2/1993 | Weiss ..................... | 128/419 |
| 5,199,429 A | 4/1993 | Kroll et al. .............. | 128/419 |
| 5,395,395 A | 3/1995 | Hedberg .................. | 607/7 |
| 5,411,525 A | 5/1995 | Swanson et al. ........ | 607/5 |
| 5,466,254 A | 11/1995 | Helland .................. | 607/123 |
| 5,507,781 A | 4/1996 | Kroll et al. .............. | 607/7 |
| 5,527,346 A | 6/1996 | Kroll ...................... | 607/5 |
| 5,662,689 A | 9/1997 | Elsberry et al. ......... | 607/5 |
| 5,733,310 A * | 3/1998 | Lopin et al. ............. | 607/7 |
| 5,792,187 A | 8/1998 | Adams .................... | 607/5 |
| 5,833,712 A | 11/1998 | Kroll et al. .............. | 607/7 |

(List continued on next page.)

OTHER PUBLICATIONS

Walcott, Gregory P. M.D., et al., Choosing the Optimal Monophasic and Biphasic Waveforms for Ventricular Defibrillation, Journal of Cardiovascular Electrophysiology, vol. 6, No. 9, pp: 737–750 (Sep. 1995).

Pearce, J.A., et al., Myocardial Stimulation with Ultrashort Duration Current Pulses, PACE, vol. 5, pp: 52–58 (Jan.–Feb. 1982).

Kroll, Mark W., A Minimal Model of the Single Capacitor Biphasic Defibrillation Waveform, PACE, vol. 17, Part 1, pp: 1782–1792 (Nov. 1994).

(List continued on next page.)

Primary Examiner—Kennedy Schaetzle

(57) ABSTRACT

A shocking circuit is provided for use in an ICD for generating rounded multi-step defibrillation shocking pulse waveforms having reduced voltage peaks to minimize pain within a patient receiving the shocking pulse. The shocking circuit includes a set of capacitors, a resistive-capacitive (RC) filter, and low pain waveform control unit for selectively discharging the capacitors through the RC filer to generate the rounded pulse waveform. In one example, a pair capacitors are provided for generating a two-step pulse. The low pain waveform control unit initially discharges the capacitors in parallel to generate a first step of the pulse waveform while periodically shunting a portion of charge through the RC filter to reduce peak voltage. The low pain waveform control unit then discharges the capacitors in series to generate a second step of the pulse waveform while also periodically shunting a portion of charge through the RC filter to reduce peak voltage. With this circuit arrangement, a rounded, multi-step waveform can be readily generated for use within an ICD without requiring a high voltages or large capacitors. The shocking pulse itself is generated so as to approximate an input rounded waveform having an initial portion that increases monotonically to a final rounded peak, then decreases sharply.

18 Claims, 21 Drawing Sheets

U.S. PATENT DOCUMENTS

| | | | |
|---|---|---|---|
| 5,906,633 A | 5/1999 | Mouchawar et al. | 607/5 |
| 5,913,877 A | 6/1999 | Kroll et al. | 607/5 |
| 6,041,254 A | 3/2000 | Sullivan et al. | 607/5 |
| 6,091,989 A | 7/2000 | Swerdlow et al. | 607/5 |
| 6,167,305 A | 12/2000 | Cammilli et al. | 607/5 |
| 6,233,483 B1 | 5/2001 | Causey, III et al. | 607/5 |
| 6,405,081 B1 * | 6/2002 | Lyster et al. | 607/5 |

OTHER PUBLICATIONS

Blair, H.A., On the Intensity–Time Relations for Stimulation By Electric Currents. I, Journal of General Physiology, vol. 15, No. 6, pp: 709–729 (Jul. 20, 1932).

Blair, H.A., On the Intensity–Time Relations for Stimulation by Electric Currents. II, Journal of General Physiology, vol. 15 No. 6, pp: 731–755 (Jul. 20, 1932).

Harbison, Mark T., et al., Patient Discomfort After Transvenous Catheter Cardioversion of Atrial Tachyarrhythmias with Rounded Waveforms–Initial Results, Circulation Suppl., vol. 94, No. 8, Abstract No. 386 (Oct. 15, 1996).

Harbinson, M.T., et al., Rounded Biphasic Waveform Reduces Energy Requirements for Transvenous Catheter Cardioversion of Atrial Fibrillation and Flutter, PACE, vol. 20, Part II, pp: 226–229 (Jan. 1997).

Ammer, Richard, et al., Pain Threshold for Low Energy Intracardiac Cardioversion of Atrial Fibrillation with Low or No Sedation, PACE, vol. 20, Part II, pp: 230–236 (Jan. 1997).

Neri, Roberto, et al., Effect of Electrode Configuration and Capacitor Size on Internal Atrial Defibrillation threshold Using Leads Currently Used for Ventricular Defibrillation, Jour. oF Interventional Cardiac Electrophysiology, 3:149–153 (1999).

Borinai, Giuseppe, M.D., et al., Transvenous Internal Cardioversion for Atrial Fibrillation: a Randomized Study on Defibrillation Threshold and Tolerability of Asymmetrical Compared with Symmetrical Shocks, Int. Journal of Cardiology, vol. 71, pp: 63–69 (1999).

Lok, Ngai–Sang, MB, et al., Clinical Shock Tolerability and Effect of Different Right Atrial Electrode Locations on Efficacy of Low Energy Human Transvenous Atrial Defibrillation Using an Implantable Lead System, JACC, vol. 30, No. 5, pp:1324–1230 (Nov. 1, 1997).

Tomassoni, Gery, M.D., et al., Testing Different Biphasic Waveforms and Capacitances: Effect on Atrial Defibrillation Threshold and Pain Perception, JACC, vol. 28, No. 3, pp: 695–699 (Sep. 1996).

* cited by examiner

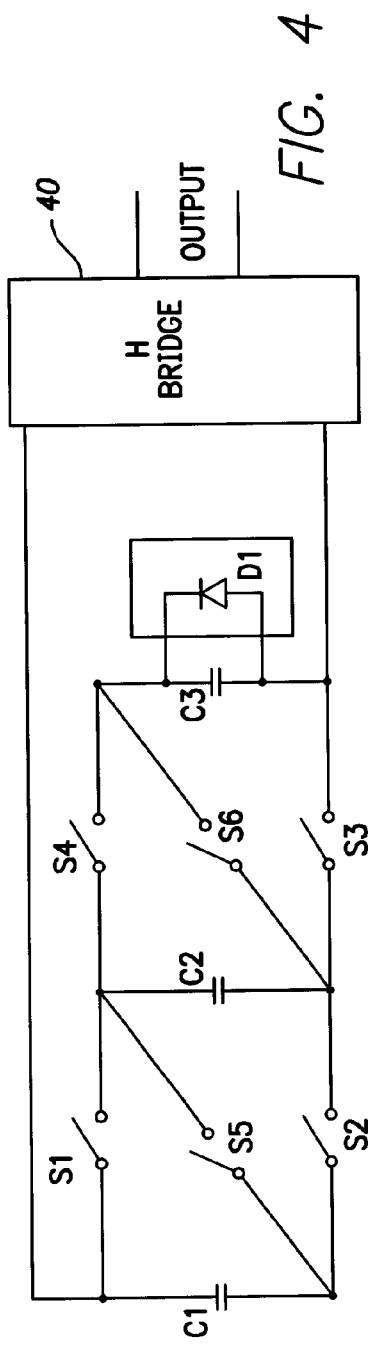
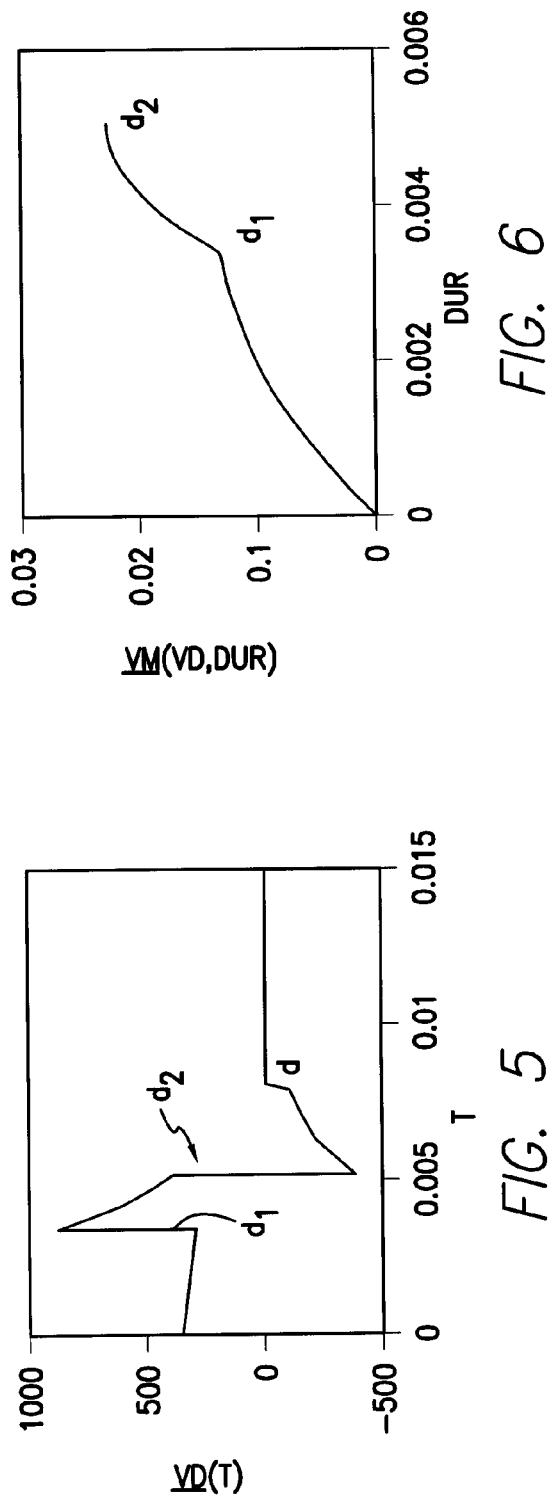
FIG. 4
FIG. 5
FIG. 6

FIG. 15

| $T_m$ 2 ms | $d_1^{opt}$[ms] $d_2^{opt}$[ms] $c_A(=c_B)$[μF] | $R_S$ [ohms] | | | |
|---|---|---|---|---|---|
| | | 30 | 50 | 70 | 90 |
| | 30 | 1.286 | 1.508 | 1.640 | 1.729 |
| | | 0.422 | 0.647 | 0.842 | 1.014 |
| | 60 | 1.581 | 1.763 | 1.862 | 1.923 |
| | | 0.747 | 1.094 | 1.377 | 1.618 |
| | 90 | 1.729 | 1.879 | 1.956 | 2.003 |
| | | 1.014 | 1.441 | 1.778 | 2.058 |

FIG. 16

| $T_m$ 3 ms | $d_1^{opt}$[ms] $d_2^{opt}$[ms] $c_A(=c_B)$[μF] | $R_S$ [ohms] | | | |
|---|---|---|---|---|---|
| | | 30 | 50 | 70 | 90 |
| | 30 | 1.655 | 2.000 | 2.219 | 2.372 |
| | | 0.443 | 0.693 | 0.918 | 1.121 |
| | 60 | 2.120 | 2.433 | 2.612 | 2.728 |
| | | 0.808 | 1.216 | 1.562 | 1.863 |
| | 90 | 2.372 | 2.645 | 2.792 | 2.885 |
| | | 1.121 | 1.641 | 2.066 | 2.427 |

FIG. 17

| $T_m$ 4 ms | $d_1^{opt}$[ms] $d_2^{opt}$[ms] $c_A(=c_B)$[μF] | $R_S$ [ohms] | | | |
|---|---|---|---|---|---|
| | | 30 | 50 | 70 | 90 |
| | 30 | 1.950 | 2.408 | 2.710 | 2.928 |
| | | 0.454 | 0.720 | 0.963 | 1.188 |
| | 60 | 2.573 | 3.016 | 3.280 | 3.458 |
| | | 0.844 | 1.294 | 1.683 | 2.029 |
| | 90 | 2.928 | 3.331 | 3.557 | 3.704 |
| | | 1.188 | 1.773 | 2.264 | 2.689 |

FIG. 26

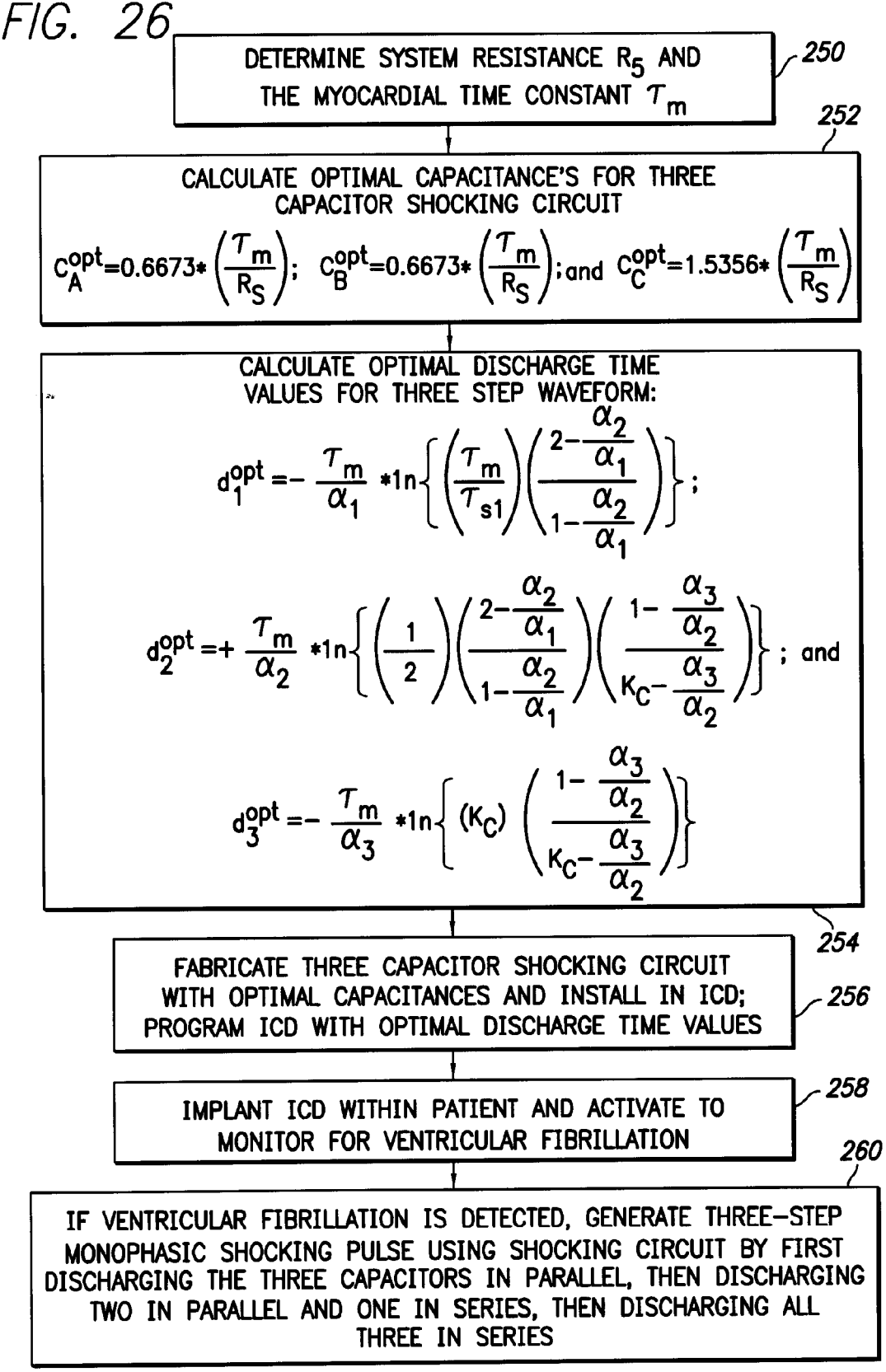

250 DETERMINE SYSTEM RESISTANCE $R_S$ AND THE MYOCARDIAL TIME CONSTANT $T_m$

252 CALCULATE OPTIMAL CAPACITANCE'S FOR THREE CAPACITOR SHOCKING CIRCUIT $$C_A^{opt}=0.6673*\left(\frac{T_m}{R_S}\right); \quad C_B^{opt}=0.6673*\left(\frac{T_m}{R_S}\right); \text{ and } C_C^{opt}=1.5356*\left(\frac{T_m}{R_S}\right)$$

254 CALCULATE OPTIMAL DISCHARGE TIME VALUES FOR THREE STEP WAVEFORM:

$$d_1^{opt}=-\frac{T_m}{\alpha_1}*\ln\left\{\left(\frac{T_m}{T_{s1}}\right)\left(\frac{2-\frac{\alpha_2}{\alpha_1}}{1-\frac{\alpha_2}{\alpha_1}}\right)\right\};$$

$$d_2^{opt}=+\frac{T_m}{\alpha_2}*\ln\left\{\left(\frac{1}{2}\right)\left(\frac{2-\frac{\alpha_2}{\alpha_1}}{1-\frac{\alpha_2}{\alpha_1}}\right)\left(\frac{1-\frac{\alpha_3}{\alpha_2}}{K_C-\frac{\alpha_3}{\alpha_2}}\right)\right\}; \text{ and}$$

$$d_3^{opt}=-\frac{T_m}{\alpha_3}*\ln\left\{(K_C)\left(\frac{1-\frac{\alpha_3}{\alpha_2}}{K_C-\frac{\alpha_3}{\alpha_2}}\right)\right\}$$

256 FABRICATE THREE CAPACITOR SHOCKING CIRCUIT WITH OPTIMAL CAPACITANCES AND INSTALL IN ICD; PROGRAM ICD WITH OPTIMAL DISCHARGE TIME VALUES

258 IMPLANT ICD WITHIN PATIENT AND ACTIVATE TO MONITOR FOR VENTRICULAR FIBRILLATION

260 IF VENTRICULAR FIBRILLATION IS DETECTED, GENERATE THREE-STEP MONOPHASIC SHOCKING PULSE USING SHOCKING CIRCUIT BY FIRST DISCHARGING THE THREE CAPACITORS IN PARALLEL, THEN DISCHARGING TWO IN PARALLEL AND ONE IN SERIES, THEN DISCHARGING ALL THREE IN SERIES

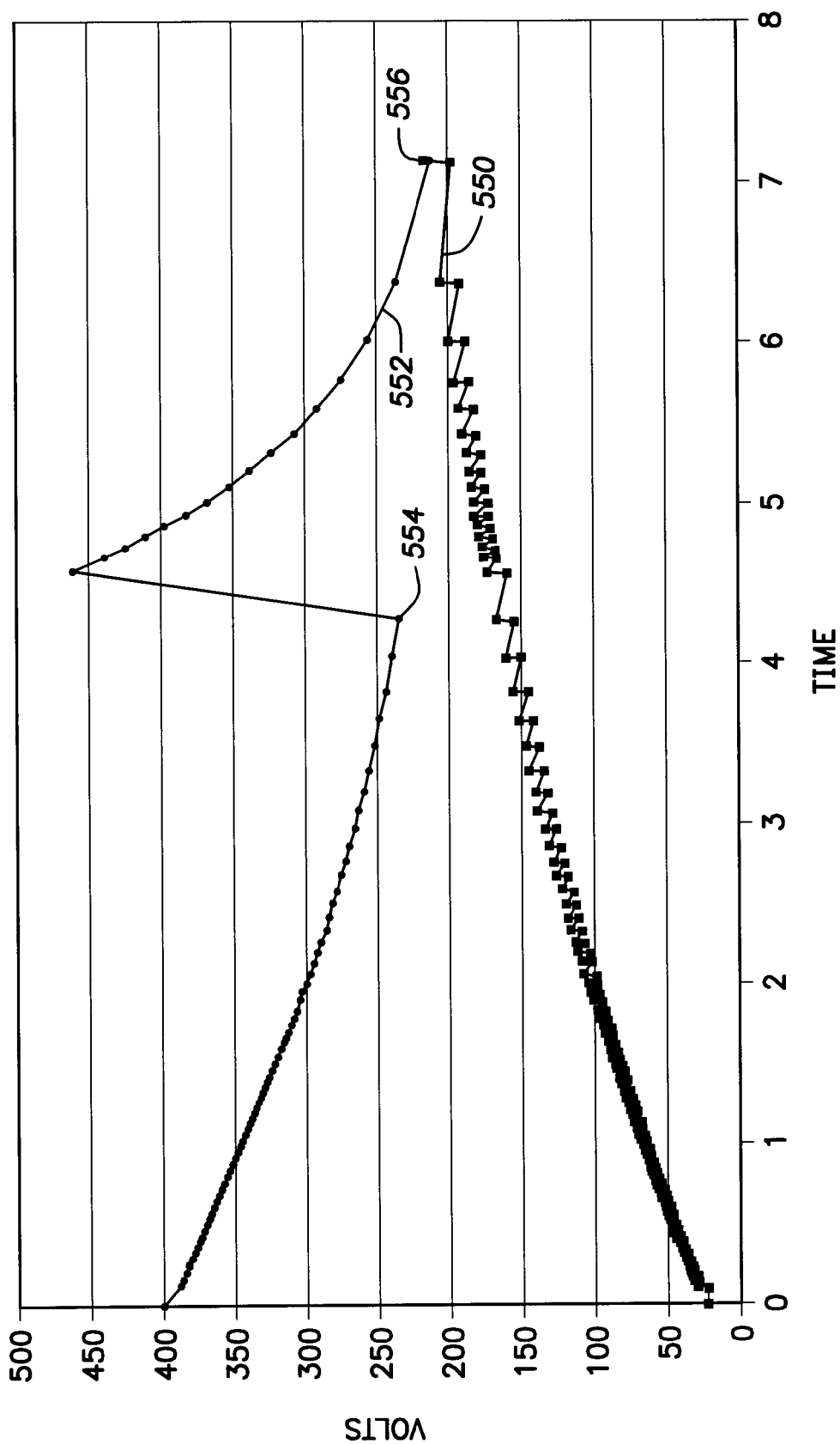

SYSTEM AND METHOD OF GENERATING A LOW-PAIN MULTI-STEP DEFIBRILLATION WAVEFORM FOR USE IN AN IMPLANTABLE CARDIOVERTER/ DEFIBRILLATOR (ICD)

CROSS-REFERENCE TO RELATED APPLICATIONS

This application is a Continuation-in-Part (CIP) of U.S. patent application Ser. No. 09/803,271, filed Mar. 9, 2001, (now U.S. Pat. No. 6,484,056, issued Nov. 19, 2002) which claimed the benefit of U.S. patent application Ser. No. 09/073,394, filed May 5, 1998 (now U.S. Pat. No. 6,233,483 B1, issued May 15, 2001), which in turn had claimed the benefit of U.S. Provisional Patent Application No. 60/046, 610, filed May 15, 1997.

FIELD OF THE INVENTION

The present invention relates to implantable medical devices, and more particularly to an implantable cardioverter defibrillator (ICD) configured to provide a low pain defibrillation waveform.

BACKGROUND OF THE INVENTION

An ICD continues to be a relatively large device for implantation in the human body. The size of the ICD is primarily determined by the battery and capacitors used therein. The size of the battery (or batteries, in some instances) and capacitors, in turn, is determined by the shock energy requirements for a defibrillation pulse. Thus, a design approach that reduces the energy requirements for defibrillation results in a direct reduction in the overall ICD size.

In existing ICD devices, the defibrillation waveform or pulse used to deliver a defibrillation shock to the heart is generated by first charging the equivalent of a single capacitor (most ICDs use two capacitors connected in series to function as a single capacitor, thereby reducing the working voltage requirements for each capacitor of the series stack, as explained below) to a desired charge level (voltage) and then discharging the single capacitor through the cardiac tissue for a prescribed period of time during a first or positive phase of the defibrillation waveform, and then reversing the polarity of the discharge for a second prescribed period of time during a second or negative phase of the defibrillation waveform, thereby producing a biphasic stimulation pulse or waveform. It should be noted that in this context the term "single capacitor" is used to refer to a single capacitance, which may be, and usually is obtained by a hardwired connection of two capacitors in series such that the two series capacitors always function and act as though they were a single capacitor. (Two or more capacitors are connected in series in this manner in order to achieve a higher working voltage for the series-connected capacitor. That is, when two capacitors are connected in series, and each has a working voltage of, e.g., 375 volts (V), then the overall or total working voltage of the series combination becomes 750 V.)

The purpose of applying a defibrillation shock to the heart is to shock the heart out of a state of fibrillation, or other non-functional state, into a functional state where it may operate efficiently as a pump to pump blood through the body. To this end, the positive phase of the biphasic waveform is preferably a very high voltage that serves to synchronously capture as many heart membrane cells as possible. See, Kroll, "A minimum model of the signal capacitor biphasic waveform" Pace, November 1994. The negative phase of the biphasic waveform, in contrast, simply serves to remove the residual electrical charge from the membrane cells and bring the collective membrane voltage back to its original position or value. See, e.g., Kroll, supra; Walcott, et al., "Choosing The Optimal Monophasic and Biphasic Wave-Forms for Ventricular Defibrillation", Journal of Cardiovascular Electrophysiology (September 1995). A biphasic pulse generator of the type used in an ICD device is shown, e.g., in U.S. Pat. No. 4,850,357, issued to Bach, Jr.; and U.S. Pat. No. 5,083,562, issued to de Coriolis et al.

When a voltage shock is first applied to a membrane cell, the membrane does not respond to the shock immediately. Rather, the cell response lags behind the applied voltage. This time lag is more or less predictable in accordance with the Blair membrane model. See, e.g., Blair, "On the intensity-time relations for stimulation by electric currents I", J. Gen Physiol., Vol.15, pp. 709–729 (1932), and Blair, "On the intensity time relations for stimulation by electric currents II", J. Gen Physiol., Vol. 15, pp. 731–755 (1932); Pearce et al., "Myocardial stimulation with ultrashort duration current pulses," PACE, Vol. 5, pp. 52–58 (1982). When the applied voltage comprises a biphasic pulse having a constant voltage level for the duration of the positive phase (a condition achievable only when the voltage originates from an ideal battery), the membrane cell response to the positive phase reaches a peak (i.e., is at an optimum level) at the trailing edge of the positive phase. Unfortunately, when the applied voltage originates from a charged capacitor, as is the case for an ICD device, the applied voltage waveform does not remain at a constant voltage level, but rather has a significant "tilt" or discharge slope associated therewith. Such tilt or slope causes the peak membrane cell response to occur at some point prior to the trailing edge of the positive phase, which is less than optimum. What is needed, therefore, is a way to optimize the applied voltage waveform so that a maximum membrane cell response occurs coincident with, or nearly coincident with, the trailing edge of the positive phase.

It is known in the art to switch the capacitors of an ICD from a parallel configuration during the positive phase of a biphasic defibrillation pulse to a series configuration during the negative phase of the biphasic defibrillation pulse. See, e.g., U.S. Pat. No. 5,199,429 (FIG. 7A) and U.S. Pat. No. 5,411,525. While such action produces a defibrillation waveform having a somewhat different shape, i.e., a waveform having a leading edge voltage of the second or negative phase which is approximately twice the trailing edge voltage of the first or positive phase, such action does little to achieve a maximum cell membrane response coincident with the trailing edge of the first or positive phase.

It is also known in the art to sequentially switch capacitors in an ICD device in order to allow waveform "tailoring", e.g., prolong the positive phase duration by sequentially switching in a second charged capacitor as shown in FIG. 6A of U.S. Pat. No. 5,199,429, or by sequentially switching in second, third and fourth charged capacitors, as shown in FIG. 6C of U.S. Pat. No. 5,199,429. However, such "tailoring" still does not address the main concern of achieving a maximum cell membrane response coincident with the trailing edge of the positive phase.

It is thus evident that what is needed is a capacitor switching scheme and/or method for use within an ICD device which achieves a maximum cell membrane response near or coincident with the trailing edge of the positive phase.

It is also desirable to provide an ICD that is as small as possible. The limiting factor on ICD thickness is the diameter of the high-energy capacitors. As indicated above, current ICDs typically use two electrolytic capacitors. Current technology in electrolytic capacitors limits the stored voltage to about 450 V per capacitor. Therefore, the current approach is to use two large (200 µF or more) capacitors to achieve the stored energy of 25J–40J required for defibrillation. Therefore, the thickness of the ICD is determined by the thickness of the large capacitors. There is thus a need for an ICD construction, which would permit the needed energy for defibrillation to be stored in the ICD, while allowing a thinner ICD thickness.

The inventions described in predecessor U.S. patent application Ser. No. 09/073,394 advantageously address the above and other needs. In particular, that patent application described a technique for generating a highly efficient biphasic defibrillation pulse by switching at least two charged capacitors from a parallel connection to various combinations of a parallel/series connection or a series connection during the first phase of the defibrillation pulse. A stepped-up voltage during the first phase, in turn, gives an extra boost to, and thereby forces additional charge (current) into, the cardiac tissue cells, and thereby transfers more charge to the membrane of the excitable cardiac cell than if the capacitors were continuously discharged in series. Phase reversal is timed with the cell membrane reaching its maximum value at the end of the first phase.

The inventions described in U.S. patent application Ser. No. 09/976,603 are directed to achieving still other advantages. More specifically, the inventions of that patent application were directed techniques for generating a defibrillation waveform that requires even less shock energy to reach the myocardial defibrillation threshold so that battery power can be saved and device longevity improved, while still providing effective defibrillation. Techniques were also described for generating a defibrillation waveform that reduces the total time required to reach the myocardial defibrillation threshold thereby permitting the patient to be defibrillated more quickly.

Although the techniques of the predecessor patent applications are quite effective in generating a wide variety of useful defibrillation waveforms, room for further improvement remains. A significant problem with conventional defibrillation techniques is the defibrillation pulses cause substantial pain to the patient. In many cases, the patient is unconscious by the time the shock is administered and hence the pain is experienced upon the patient regaining consciousness. In other cases, however, the shock is administered while the patient is still conscious. In either case, it would be highly desirable to reduce the pain experienced by the patient.

U.S. Pat. No. 5,906,633 entitled "System for Delivering Rounded Low Pain Therapeutic Electrical Waveforms To The Heart" by Mouchawar et al. provides various systems and techniques for reducing patient pain by eliminating sharp voltage peaks in the shocking pulse waveform. More specifically, the patent describes a system for delivering a low pain waveform that is biphasic and has rounded leading and trailing edges. The rounded leading and trailing edges are believed to decrease the discomfort experienced by the patient. In one embodiment, the circuit has two capacitors connected in parallel with one another and with an H-bridge. The two capacitors are connected via a switch that can be closed so as to simultaneously charge one capacitor from the other while simultaneously applying voltage to the H-bridge. The circuit also includes a dump resistor that can be connected in parallel with the capacitors so as to increase the rounding of the trailing edges of the waveform. In another embodiment, controllable switches can also be included so as to be able to connect the capacitors in series and apply a sharp peak defibrillation waveform to the heart. U.S. Pat. No. 5,906,633 is incorporated by reference herein in its entirety.

Although the system of U.S. Pat. No. 5,906,633 is effective is providing shocks that yield reduced pain, room for further improvement remains, particularly insofar as the generation of shocks for defibrillation is concerned. In particular, the circuit provided therein is fairly inefficient because much of the energy stored in the capacitors is not used in the shocking pulse and is instead lost as heat. Also it requires fairly large values for either voltage or power so as to achieve sufficient filtering to provide a smooth waveform shape. Alternatively, a larger capacitor can be used, but that requires larger ICD size and weight.

Accordingly, it would be desirable to provide alternative techniques for generating rounded shocking waveforms and it is to these ends that aspects of the invention of the present CIP application are directed. In particular it is desirable to exploit the stepped waveform techniques of the predecessor patent applications summarized above for generating low pain rounded waveforms and further aspects of the invention are directed to novel waveform shapes achieved thereby.

SUMMARY OF INVENTION

In accordance with a first aspect of the invention, systems and methods are provided for generating a rounded low-pain waveform formed of multiple steps or segments. In a system embodiment, a shocking circuit is provided that includes a set of capacitors, a resistive-capacitive (RC) filter, and low pain waveform control unit connected to the capacitors and operative to selectively discharge the capacitors through the RC filter to generate the rounded, multi-step defibrillation pulse waveform.

In one example, dual shocking capacitors are configured so as to be discharged either in parallel or in series during the positive phase of the pulse waveform. The low pain waveform control unit operates to first discharge the capacitors in parallel to generate a first step or portion of the positive phase of the waveform while periodically shunting a portion of charge through the RC filter to reduce the peak voltage of the first step. Then the low pain waveform control unit discharges the capacitors in series to generate a second step of the positive phase of the waveform while also periodically shunting a portion of charge through the RC filter to thereby also reduce the peak voltage of the second step. With this circuit arrangement, a rounded, multi-step waveform can readily be generated for use within an ICD without requiring a high voltages or large capacitors.

In accordance with a second aspect of the invention, systems and methods are provided for generating a shocking waveform that approximates a monotonically increasing input waveform shape. In an exemplary embodiment of the method, steps are performed so as to generate a waveform having a positive phase that approximates an input waveform shape having an initial portion increasing sharply from zero voltage to a initial voltage ($V_{initial}$), a central portion increasing exponentially from the initial voltage to a peak voltage ($V_{peak}$), and a tail portion decreasing sharply back to zero voltage. The central portion of the target waveform being approximated has an exponential shape represented by:

$$V_{waveform} = V_{initial} + (V_{peak} - V_{initial}) * (1 - e^{-t/T}).$$

The monotonically-increasing waveform is believed to be particularly effective in reducing patient pain. The monotonically-increasing waveform can be generated using the dual capacitor system summarized above configured to produce a single monotonically-increasing waveform from the two steps of the multi-step waveform to thereby achieve significant pain reduction while also gaining the benefits of the use of multi-step waveforms.

In accordance with a third aspect of the invention, systems and methods are provided for generating shocking waveforms that approximate any input waveform shape, rounded or otherwise. In a method example, a shocking waveform is generated by inputting a waveform to be approximated then increasing a magnitude of a voltage of an output shocking waveform as a function of time. The magnitude of the voltage of the shocking waveform is compared to a magnitude of the voltage of the input waveform as a function of time and, whenever the magnitude of the shocking waveform exceeds the magnitude of the voltage of the input waveform, the magnitude of the shocking waveform is decreased until it again falls below the voltage of the magnitude of the input waveform. These steps are repeated so that the magnitude of the output shocking waveform generally approximates the input waveform.

In one example, the method is employed within a defibrillator having a shocking capacitor, a resistive-capacitive (RC) filter, and a chopping switch interconnecting the shocking capacitor and the RC filter. The magnitude of the voltage of the shocking waveform is decreased whenever the magnitude of the shocking waveform exceeds the magnitude of the voltage of the input waveform by opening and closing the chopping switch so as to produce an output from the RC filter that approximates the input waveform.

With this technique, virtually any desired positive-phase waveform shape can be approximated. Preferably, the technique is employed to generate the monotonically-increasing waveform summarized above to reduce patient pain. Also preferably, the technique is exploited using the dual capacitor multistep shocking system also summarized above to permit the use of relatively small capacitors using relatively low voltages.

BRIEF DESCRIPTION OF THE DRAWINGS

The above and other aspects, features, and advantages of the present invention will be more apparent from the following more particular description thereof, presented in conjunction with the following drawings, wherein:

FIG. 4 is a simplified schematic diagram of a three-capacitor ICD made in accordance with the invention;

FIG. 5 illustrates one type of defibrillation waveform that may be generated using the ICD of FIG. 4;

FIG. 6 depicts the excitable cardiac membrane response during phase 1 (positive phase) to the waveform of FIG. 5;

FIGS. 15, 16 and 17 illustrate how the optimal values for $d_1$ and $d_2$, tissue resistance ($R_S$) and tissue time constants ($\tau_m$);

FIG. 26 is a flow chart providing an overview of a technique for making an using an ICD for generating shocking pulses exploiting the defibrillation waveform of FIG. 23.

FIG. 35 illustrates an exemplary low pain defibrillation waveform actually generated using the RC shocking circuit of FIG. 34;

DETAILED DESCRIPTION OF THE INVENTION

The following description is of the best mode currently contemplated for practicing the invention.

The basic concept of the invention relating to forming an efficient defibrillation waveform can be practiced with two or more capacitors within the ICD. The preferred number of capacitors is three. However, the basic concept will first be explained in the context of a two-capacitor ICD.

Pulse Generation Using Parallel/Series Capacitors

Figure 1:
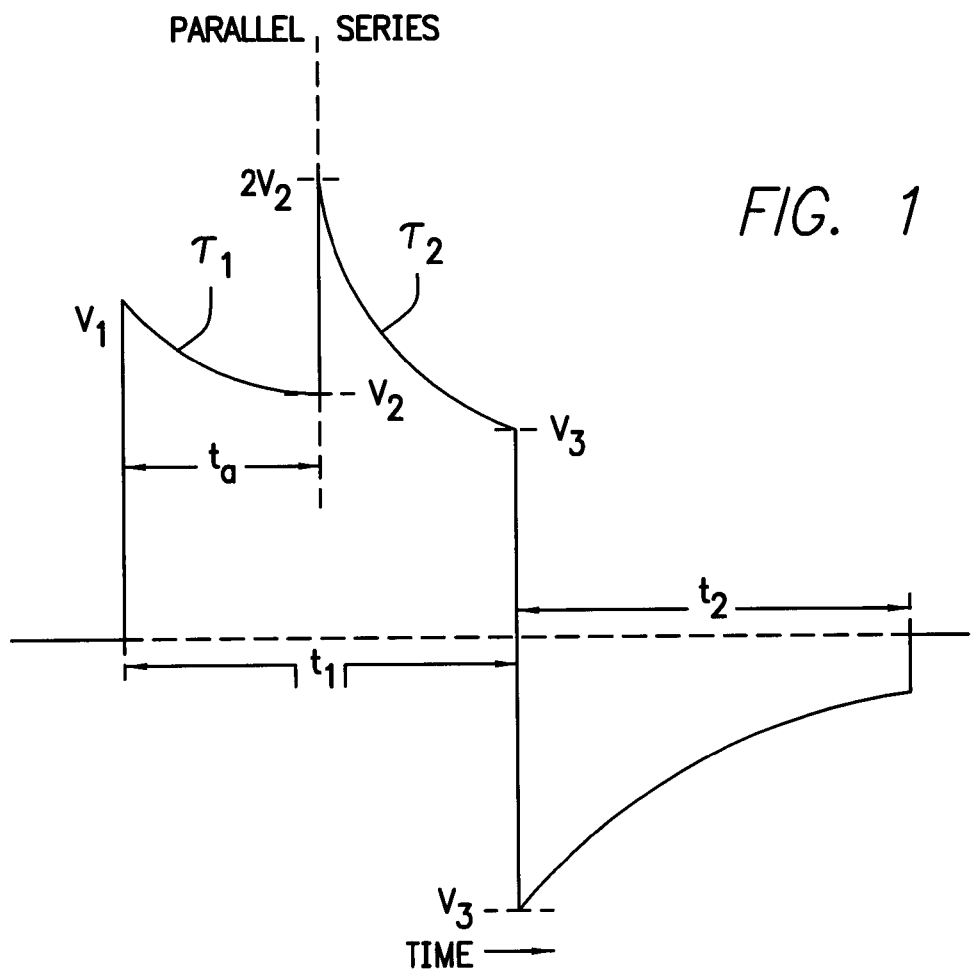
FIG. 1 illustrates a preferred defibrillation biphasic pulse or waveform generated in accordance with a two-capacitor ICD in accordance with the present invention.

In accordance with one aspect of the invention, then a biphasic pulse or waveform is generated by an ICD device having two capacitors that includes a positive phase of duration $t_1$ ms and a negative phase of duration $t_2$ ms, as shown in FIG. 1. First and second capacitors, $C_A$ and $C_B$, within the ICD device are initially charged to a voltage $V_1$ and are connected in parallel. The biphasic defibrillation pulse begins by discharging the charged parallel capacitors through the cardiac tissue by way of defibrillation electrodes in contact with the cardiac tissue. Thus, a leading edge of the biphasic pulse starts at a first peak voltage of approximately $V_1$ volts (the charge on the first and second capacitors when first connected to the electrodes).

During a first step or portion of the positive phase of the biphasic pulse, the amplitude of the biphasic pulse decays from the first peak voltage $V_1$ to a voltage $V_2$ in accordance with a first time constant $\tau_1$. The first time constant $\tau_1$ varies as a function of $(C_A+C_B)R$, where $C_A$ is the value of the first capacitor, $C_B$ is the value of the second capacitor, and R is an effective resistance associated with the discharge through the first and second electrodes.

A second step or portion of the positive phase begins by connecting the first and second capacitors in series. This sudden series connection increases the defibrillation pulse to a second peak voltage of approximately $2(V_2)$ volts (the sum of the voltages on each of the first and second capacitors at the time the series connection is made), as illustrated in FIG. 1. The amplitude of the biphasic pulse decays during the second portion of the positive phase from the second peak voltage $2(V_2)$ to a voltage $V_3$ in accordance with a second time constant $T_2$. The second time constant $T_2$ varies as a function of $(C_A C_B/C_A+C_B)R$. Advantageously, the voltage at the trailing edge of the positive phase, $V_3$, occurs at a time that is near the maximum cell membrane response.

The negative phase of the biphasic waveform begins by inverting the polarity of the series-connected first and second capacitors. Such negative phase thus commences at a third peak voltage of approximately −V3 volts, and decays thereafter towards zero in accordance with the second time constant $T_2$. After a prescribed time period $t_2$, the negative phase ends.

The biphasic waveform produced in accordance with the two-capacitor ICD is illustrated in FIG. 1. The first portion of the positive phase may terminate when either: (1) the voltage decreases below a threshold voltage $V_3$; or (2) a prescribed time period $t_a$ has elapsed.

Figure 2:
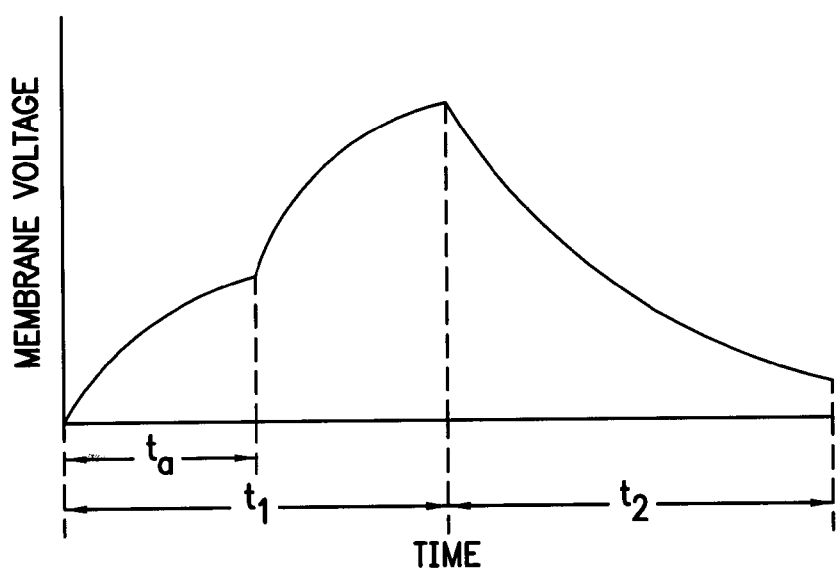
FIG. 2 depicts the excitable cardiac membrane response to the waveform of FIG. 1.

The tissue membrane voltage that results when the waveform of FIG. 1 is applied to excitable cardiac tissue membranes is as shown in FIG. 2. This membrane voltage is obtained by modeling the tissue membranes as taught in the Blair reference, previously cited. As shown in FIGS. 11–20, the optimum duration for $t_a$ will be described in more detail.

Figure 3:
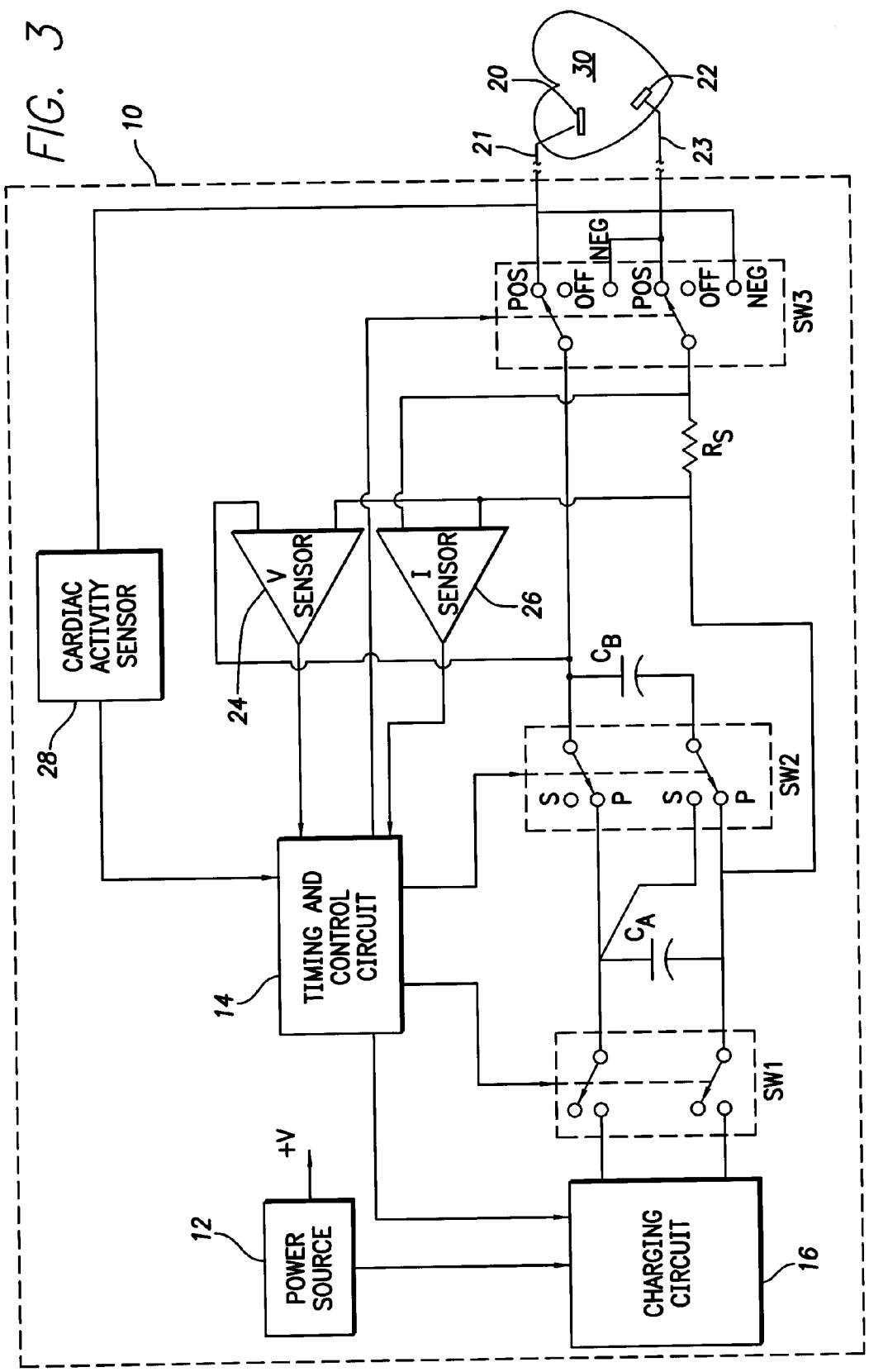
FIG. 3 is a functional block diagram of a two-capacitor ICD device, which generates the waveform of FIG. 1.

A functional block diagram of the pulse generation circuitry used to generate the biphasic waveform of the two-capacitor ICD is shown in FIG. 3.

As seen in FIG. 3, a cardiac tissue-stimulating device 10 includes a power source 12, e.g., at least one battery, a timing and control circuit 14, a charging circuit 16, an isolation switch network SW1, a series parallel switch network SW2, at least two capacitors $C_A$ and $C_B$, an output switch network SW3, and at least two electrodes 20 and 22. The electrodes 20 and 22 are adapted to be positioned within or on the heart. The electrodes 20 and 22 are connected to the output switch SW3 through conventional leads 21 and 23, respectively.

A voltage sense amplifier 24 senses the voltage held on the capacitor $C_B$ (which will be the same voltage as capacitor $C_A$ when $C_A$ and $C_B$ are connected in parallel). In some embodiments of the invention, a current sense amplifier 26 may also be used to sense the current flowing to or returning from one of the electrodes 20 or 22. In FIG. 3, such current is sensed by differentially measuring the voltage across a small current-sense resistor $R_s$ connected in series with electrode 22. The outputs of the voltage sense amplifier 24 and the current sense amplifier 26 are directed to the timing and control circuit 14.

A suitable cardiac activity sensor 28 is also employed within the device 10 in order to detect cardiac activity. The function of the sensor 28 is to sense cardiac activity so that an assessment can be made by the timing and control circuitry whether a defibrillation pulse needs to be generated and delivered to the cardiac tissue. Such sensor 28 may take many forms, e.g., a simple R-wave sense amplifier of the type commonly employed in implantable pacemakers. The details of the sensor 28 are not important for purposes of the present invention.

The power source 12 is connected to provide operating power to all components and circuitry within the device 10. The power source 12 also provides the energy needed to generate the biphasic defibrillation pulse. That is, energy stored within the power source 12 is used to charge capacitors $C_A$ and $C_B$, through the charging circuit 18, up to the desired initial defibrillation starting pulse voltage $V_1$. Such charging is carried out under control of the timing and control circuit 14. Typically, $V_1$ may be a relatively high voltage, e.g., 375 volts, even though the power source 12 may only be able to provide a relatively low voltage, e.g., 3–6 volts. The charging circuit 16 takes the relatively low voltage from the power source 12 and steps it up to the desired high voltage $V_1$, using conventional voltage step-up techniques as are known in the art. This stepped-up voltage $V_1$ is then applied through the isolation switch SW1 to both capacitors $C_A$ and $C_B$ at a time when $C_A$ and $C_B$ are connected in parallel, i.e., when SW2 is in its P position, and at a time when the output switch is in its open, or OFF, position. As the capacitors $C_A$ and $C_B$ are being charged, the voltage sense amplifier 24 monitors the voltage level on the capacitors. When the desired voltage $V_1$ has been reached, the timing and control circuitry 14 turns off the charging circuit 16 and opens the isolation switch SW1, thereby holding the voltage $V_1$ on capacitors $C_A$ and $C_B$ until such time as a defibrillation pulse is needed.

When a defibrillation pulse is called for by the timing and control circuit 14, the output switch SW3 is placed in its positive phase position, POS, thereby connecting the parallel connected capacitors $C_A$ and $C_B$ (on which the starting voltage $V_1$ resides) to the cardiac tissue through the electrodes 20 and 22. Such connection starts the discharge of capacitors $C_A$ and $C_B$ through the cardiac tissue in accordance with the first time constant $\sigma_1$ as described above in connection in FIG. 1.

After a period of time $t_a$, or as soon as the voltage across the parallel-connected capacitors CA and CB has decreased to the threshold value $V_2$ (as sensed by the voltage sense amplifier 24), the timing and control circuit switches SW2 to its series-connected or S position, thereby connecting the capacitors $C_A$ and $C_B$ in series across the electrodes 20 and 22. Such series connection doubles the voltage across the electrodes 20 and 22 to a value of $2(V_2)$. Thereafter, the discharge of the series-connected capacitors $C_A$ and $C_B$ continues through the cardiac tissue in accordance with the second time constant $\tau_2$ as described above. This discharge continues until the end of the positive phase.

The positive or first phase ends at a time $t_1$ from the beginning of the positive phase (as measured by timing circuits within the timing and control circuit 14), or when the voltage has decayed to a value $V_3$ (as sensed by voltage sense amplifier 24). Alternatively, the positive phase may end as a function of the sensed current (as sensed by the current sense amplifier 26), e.g., at a time when the sensed current has decreased from a peak value by a prescribed amount or percentage.

As soon as the positive phase ends, the timing and control circuit 14 switches the output switch SW3 to the negative phase position, NEG, thereby reversing the polarity of the discharge of the series-connected capacitors $C_A$ and $C_B$ through the cardiac tissue. The negative phase lasts thereafter for a time period $t_2$ determined by the timing and control circuitry.

The functions represented by the functional block diagram of FIG. 3 may be implemented by those of skill in the art using a wide variety of circuit elements and components. It is not intended that the present invention be directed to a specific circuit, device or method; but rather that any circuit, device or method which implements the functions described above in connection with FIG. 3 to produce a defibrillation waveform of the general type shown in FIG. 1 be covered by the invention.

Turning next to FIG. 4, there is shown a simplified schematic diagram of an ICD having three 120 µF capacitors C1, C2 and C3. The manner of charging the capacitors while they are connected in parallel is the same or similar to that shown in FIG. 3. When the capacitors C1, C2 and C3 have been charged to a high voltage, e.g., 370 V, a stored energy of approximately 25 joules is realized. Once the capacitors have been charged by the ICD, the capacitors are configured for a parallel discharge. This is accomplished by closing switches S1, S2, S3 and S4, while maintaining switches S5 and S6 open. The parallel discharge takes place from time t=0 until a time $d_1$. Once $d_1$ elapses, one of two options may be used to discharge the remaining charge.

In accordance with a first option, or Option 1, after $d_1$ has elapsed (i.e., after the capacitors are discharged in parallel until time $d_1$), all of the capacitors are discharged in series for the remainder of the pulse. This is accomplished by opening S1, S2, S3 and S4 and closing S5 and S6. At a later time, $d_2$, the "H Bridge" circuit 40 (FIG. 4) is used to reverse the polarity of the output. At yet a later time, d, the output pulse is truncated.

The waveform generated in accordance with Option 1 is illustrated in FIG. 5. The tissue membrane voltage associated with the waveform of FIG. 5 is modeled and computed, using the Blair model, as shown in FIG. 6. For the example shown in FIGS. 5 and 6, the optimum value of $d_1$ is nominally about 3.5 ms. The optimum choice of $d_2$ is when the elapsed time at $d_2$ is about 1.5 times the elapsed time at $d_1$, or when the elapsed time at $d_2$ (from t=0) is about 5.25 ms.

Figure 7:
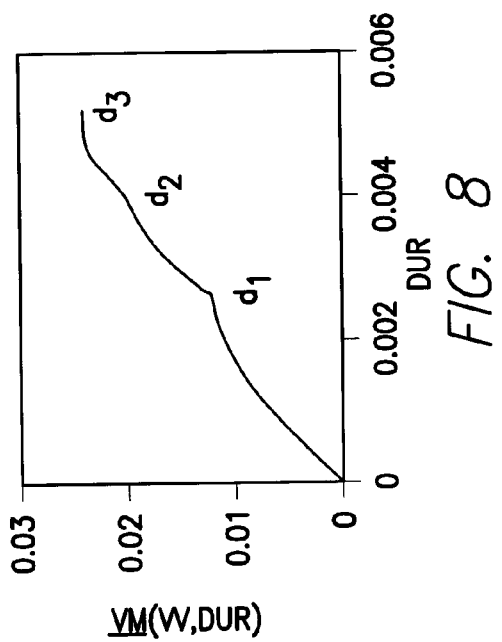
FIG. 7 illustrates another type of defibrillation waveform that may be generated using the ICD of FIG. 4.

In accordance with a second option, or Option 2, the capacitors C1 and C2 remain in parallel and are in series with C3 until time $d_2$. This is accomplished by opening S3 and S4 and closing S6. After $d_2$ all the capacitors are in series (S1 and S2 also open, S5 closed) until C3 runs out of charge at a time $d_4$. After $d_4$, the diode $D_1$ bypasses the depleted capacitor and the time constant of discharge is of C1 and C2 in series. At a time $d_3$, where $d_2 < d_3 < d_4$, the polarity of the output is reversed using the H Bridge 40. The pulse is truncated at time d. The resulting waveform is shown in FIG. 7. The resulting membrane voltage is modeled and computed and is shown in FIG. 8.

Figure 8:
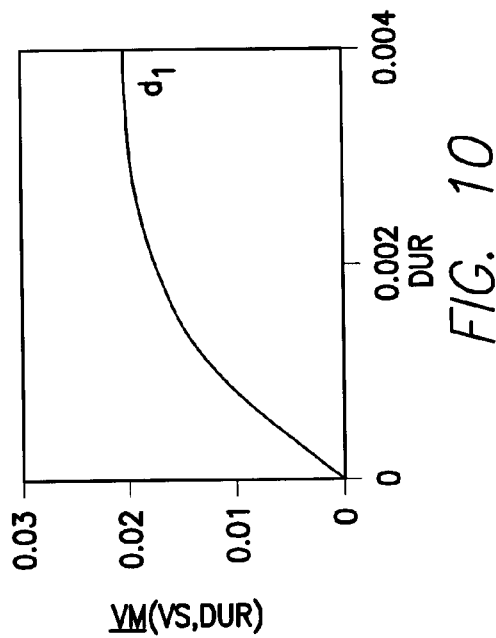
FIG. 8 depicts the excitable cardiac membrane response during phase 1 (positive phase) to the waveform of FIG. 7.

For the example shown in FIGS. 7 and 8, the optimum values of $d_1$ is 2.7 ms, $d_2$ is 1.5 times $d_1$ (or about 4 ms), $d_3$ is $d_2$+1.25 ms. The value of $d_4$ is computed to be about 7.6 ms. The choice of d can be in the range of 1.5 to 2.0 times that of $d_3$.

With either Option 1 or Option 2, the choice of the values $d_1$, $d_2$ and $d_3$ are primarily functions of the ICDs capacitance value, the discharge pathway impedance, and the tissue time constant ($\tau_m$).

The advantage of Option 2 is that the peak waveform voltage is lower than Option 1 yet a minute increase in membrane voltage over Option 1 is achieved. However, Option 1 is simpler to implement and diode $D_1$ is not needed since all the capacitors are discharged equally.

Figure 9:
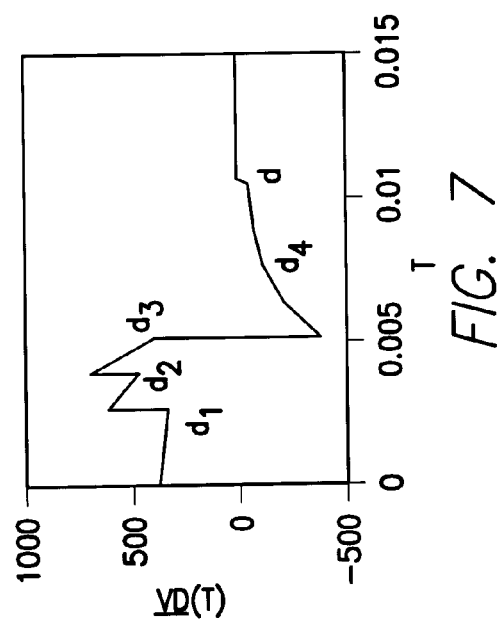
FIG. 9 illustrates, for comparative purposes, the biphasic defibrillation waveform typically provided by a two-capacitor ICD of the prior art.
Figure 10:
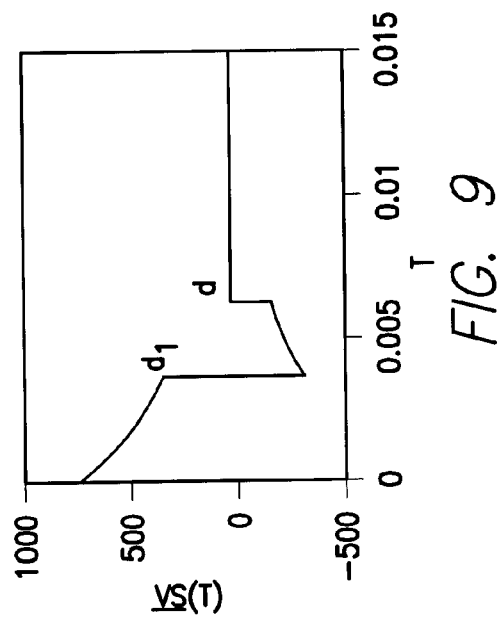
FIG. 10 illustrates, again for comparative purposes, the membrane response during phase 1 (positive phase) to the waveform of FIG. 9.

The advantages of either Option 1 or Option 2 are better appreciated by comparing the results of such discharge, as presented in FIGS. 5, 6, 7 and 8, with the corresponding discharge achieved with a two-capacitor ICD series discharge, as is commonly used in a conventional ICD of the prior art. The discharge waveform achieved with a conventional two-capacitor ICD using series discharge, and the resulting membrane voltage, is shown in FIGS. 9 and 10, respectively. Note, that to store equal energy to the three capacitor ICD, each capacitor of the two-capacitor ICD must have 1.5 times the capacitance value, or two capacitors each with C=180 µF.

As can be seen from a comparison of FIGS. 9 and 10 with FIGS. 5 and 6 (Option 1), and 5A and 5B (Option 2), for equal stored energy, the value of the peak membrane voltage for Option 2 is 1.18 times higher than the membrane voltage realized using the conventional waveform. Similarly, Option 1 yields a membrane voltage that is 1.17 times higher than is realized using the conventional waveform. In other words, a 25 joule ICD with three 120 µF capacitors and a switching network as in Option 2 performs equally to a 34.4 joule conventional ICD with two 180 µF capacitors. This represents a remarkable improvement in performance.

Figure 11:
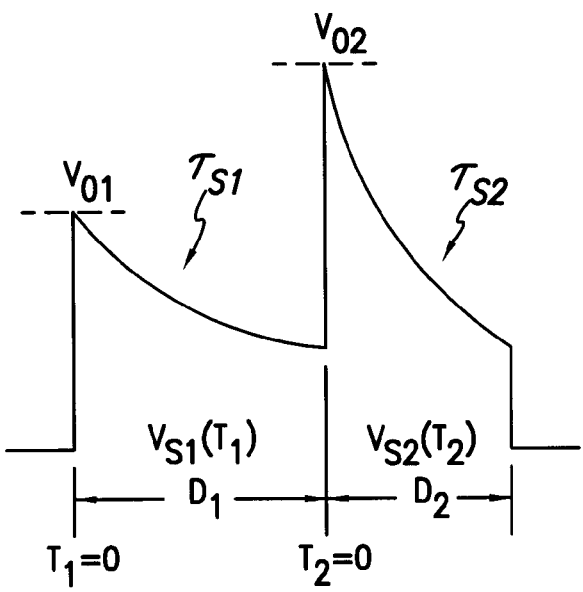
FIG. 11 shows the first phase of a parallel/series discharge waveform with the durations and time constants defined.

As shown in FIG. 11, the two-step waveform has been reproduced. Although identical in nature to that shown in FIG. 1, the designators have been changed slightly for purposes of the in depth analysis that will follow.

As described above in conjunction with FIG. 3, two capacitors, $C_A$ & $C_B$, have been charged to the same initial voltage, $V_{01}$. The system resistance (as seen by device) is given by $R_s$. For purposes of this discussion, the myocardium has been modeled as a parallel-RC circuit with myocardial tissue time constant, $\tau_m$.

The amplitude of each step of the positive portion of the defibrillation waveform, shown in FIG. 11, can be characterized with the following basic equations:

$$V_{s1}(t_1) = V_{01} \cdot \exp[-t_1/\tau_{s1}] \quad 0 \leq t_1 \leq d_1$$

$$V_{s2}(t_2) = V_{02} \cdot \exp[-t_2/\tau_{s2}] \quad 0 \leq t_2 \leq d_2$$

wherein:

$V_{s1}$ is the exponential decay during the first period, $t_1$, (i.e., Step1);

$V_{s2}$ is the exponential decay during the second period, $t_2$, (i.e., Step2);

$\tau_{s1}$ is the time constant of $C_A$ and $C_B$ in parallel;

$\tau_{s2}$ is the time constant of $C_A$ and $C_B$ in series;

$V_{o1}$ is the initial voltage during Step1 on the capacitors $C_A$ and $C_B$ once fully charged to the source voltage, $V_{o1}$; and $V_{o2}$ is the initial voltage during Step2 remaining on the capacitors $C_A$ and $C_B$, now configured in series.

The analysis that follows directly will explain how to determine the absolute and approximate solutions for the optimal durations, $d_1$ and $d_2$, to maximize induced myocardial potential, $V_m(t)$, when the two capacitors are arranged in a parallel-series, two-step arrangement.

Consider the myocardial responses to $V_{s1}(t_1)$ [Step1] and $V_{s2}(t_2)$ [Step2] separately. Note that the following derivations (Equations 1–4) make absolutely no assumptions regarding any specific relationships between the characteristics of Step1 and Step2.

The "Step1" myocardial response, $V_{m1}$, to the Step1 waveform, $V_{s1}$, is described by:

$$\frac{dV_{m1}(t_1)}{dt_1} + \frac{V_{m1}(t_1)}{\tau_m} \propto \frac{V_{s1}(t_1)}{\tau_m} \quad \text{(Eq. 1)}$$

with the initial condition: $V_{m1}(0)=0$.

The solution to this differential equation is:

$$V_{m1}(t_1) = \begin{cases} \frac{V_{01}}{\alpha_1} \cdot \left( \exp\left[\frac{-t_1}{\tau_{s1}}\right] - \exp\left[\frac{-t_1}{\tau_m}\right] \right) & \tau_{s1} \neq \tau_m \\ \frac{V_{01}}{\tau_{s1}} \cdot \left( t_1 \cdot \exp\left[\frac{-t_1}{\tau_{s1}}\right] \right) & \tau_{s1} = \tau_m \end{cases} \quad \text{(Eq. 2)}$$

where $\alpha_1 = 1 - (\tau_m/\tau_{s1})$.

The "Step2" myocardial response, $V_{m2}$, to the Step2 waveform, $V_{s2}$, is governed by:

$$\frac{dV_{m2}(d_1, t_2)}{dt_2} + \frac{V_{m2}(d_1, t_2)}{\tau_m} \propto \frac{V_{s2}(t_2)}{\tau_m} \quad \text{(Eq. 3)}$$

with the initial condition: $V_{m2}(d_1,0) = V_{m1}(d_1)$, where $d_1$ represents the final duration of Step1.

This initial condition ensures that there is a continuity of myocardial voltage when transitioning from the end of Step1 into the start of Step2.

The solution to this differential equation is:

$$V_{m2}(d_1, t_2) = V_{m1}(d_1) \cdot \exp\left[\frac{-t_2}{\tau_m}\right] + \quad \text{(Eq. 4)}$$

$$\begin{cases} \frac{V_{02}(d_1)}{\alpha_1} \cdot \left( \exp\left[\frac{-t_2}{\tau_{s2}}\right] - \exp\left[\frac{-t_2}{\tau_m}\right] \right) & \tau_{s2} \neq \tau_m \\ \frac{V_{02}(d_1)}{\tau_{s2}} \cdot \left( t_2 \cdot \exp\left[\frac{-t_2}{\tau_{s2}}\right] \right) & \tau_{s2} = \tau_m \end{cases}$$

where $\alpha_2 = 1 - (\tau_m/\tau_{s2})$, and $V_{02}$ is proportional to $V_{s2}(0)$.

Equation (4) describes a curve with a single maximum value. The step durations, $d_1 = d_1^{opt}$ and $d_2 = d_2^{opt}$, that maximize this shock-induced myocardial voltage, $V_{m2}(t_1, t_2)$, can be determined by solving the simultaneous equations given by:

$$\frac{\partial V_{m2}(d_1^{opt}, d_2^{opt})}{\partial d_1^{opt}} = 0 \qquad \frac{\partial V_{m2}(d_1^{opt}, d_2^{opt})}{\partial d_2^{opt}} = 0 \quad \text{(Eq. 5)}$$

From Equation (5), two equations that describe $d_2^{opt}$ as a function of $d_1^{opt}$ can be found (the following derivations assume $\tau_{s1} \neq \tau_m$ and $\tau_{s2} \neq \tau_m$):

$$d_2^{opt} = \frac{\tau_m}{\alpha_2} \cdot \ln \quad \text{(Eq. 6)}$$

$$\left\{ 1 + \left( \frac{\alpha_2}{\alpha_1} \cdot \frac{V_{01}}{\partial V_{02}/\partial d_1^{opt}} \right) \cdot \left( \frac{1}{\tau_{s1}} \exp\left[\frac{-d_1^{opt}}{\tau_{s1}}\right] - \frac{1}{\tau_m} \exp\left[\frac{-d_1^{opt}}{\tau_m}\right] \right) \right\}$$

$$d_2^{opt} = \quad \text{(Eq. 7)}$$

$$\frac{\tau_m}{\alpha_2} \cdot \ln \left\{ \frac{\tau_{s2}}{\tau_m} \left[ 1 - \left( \frac{\alpha_2}{\alpha_1} \cdot \frac{V_{01}}{V_{02}(d_1^{opt})} \right) \cdot \left( \exp\left[\frac{-d_1^{opt}}{\tau_{s1}}\right] - \exp\left[\frac{-d_1^{opt}}{\tau_m}\right] \right) \right] \right\}$$

Setting Equations (6) and (7) equal to each other and simplifying produces the following implicit equation for $d_1^{opt}$:

$$\left( \frac{\tau_m}{\tau_{s2}} \cdot \frac{\alpha_1}{V_{01}} \right) = \left( \frac{1/\tau_{s1}}{\partial V_{02}/\partial d_1^{opt}} + \frac{\tau_{s2}/\tau_m}{V_{02}(d_1^{opt})} \right) \exp\left[\frac{-d_1^{opt}}{\tau_{s1}}\right] - \quad \text{(Eq. 8)}$$

$$\left( \frac{1/\tau_m}{\partial V_{02}/\partial d_1^{opt}} + \frac{\tau_{s2}/\tau_m}{V_{02}(d_1^{opt})} \right) \exp\left[\frac{-d_1^{opt}}{\tau_m}\right]$$

Further simplifications of Equation (8) require that $V_{02}(d_1)$ be explicitly defined.

When the two system capacitors ($C_A$ & $C_B$) are configured into a parallel arrangement during Step1 and then reconfigured into a series arrangement during Step2, the system time constants can be explicitly defined as:

$$\tau_{s1} = R_s \cdot (C_A + C_B) \tau_{s2} = R_s \cdot (C_A C_B)/(C_A + C_B) \quad \text{(Eq. 9)}$$

Furthermore, $V_{02}(d_1)$ is explicitly defined as:

$$V_{02}(d_1) = 2 \cdot V_{s1}(d_1) \quad \text{(Eq. 10)}$$

$$= 2 \cdot V_{01} \cdot \exp[-d_1/\tau_{s1}]$$

where Equation (10) codifies the notion that, in a parallel-series arrangement, the leading edge voltage of Step2 equals twice the trailing edge voltage of Step1.

Substituting Equation (10) into Equation (8) and solving explicitly for $d_1^{opt}$ and subsequently $d_2^{opt}$ [via Equation (6) or (7)] yields:

$$d_1^{opt} = -\frac{\tau_m}{\alpha_1} \cdot \ln\left\{\left(\frac{\tau_m}{\tau_{s1}}\right)\left(\frac{2\alpha_1 - \alpha_2}{\alpha_1 - \alpha_2}\right)\right\} \quad \text{(Eq. 11)}$$

$$d_2^{opt} = +\frac{\tau_m}{\alpha_1} \cdot \ln\left\{\left(\frac{1}{2}\right)\left(\frac{2\alpha_1 - \alpha_2}{\alpha_1 - \alpha_2}\right)\right\} \quad \text{(Eq. 12)}$$

The maximum myocardial voltage attained using these optimal parallel-series step durations can then be determined by substituting Equations (10)–(12) into Equation (4) and simplifying:

$$V_{m2}(d_1^{opt}, d_2^{opt}) = V_{01}\left(\frac{1}{2}\right)^{-\frac{1}{\alpha_2}}\left(\frac{\tau_m}{\tau_{s1}}\right)^{\frac{1}{\alpha_1}-1}\left(\frac{2\alpha_1 - \alpha_2}{\alpha_1 - \alpha_2}\right)^{\frac{1}{\alpha_1}-\frac{1}{\alpha_2}} \quad \text{(Eq. 13)}$$

Note that Equations (11)–(13) are valid for any independent values of $C_A$ and $C_B$.

According to this simple RC model of defibrillation, successful defibrillation is achieved when the myocardial voltage (as embodied herein by $V_{m1}$ and $V_{m2}$) is "depolarized" to its threshold value, $V_{th}$. An equation that describes the minimum relative magnitude for $V_0$ (i.e., the voltage to which each of the capacitors is charged in preparation for the defibrillation shock) that successfully drives $V_{m2}$ to $V_{th}$ can be obtained from Equation (13) by setting $V_{m2}=V_{th}$ and solving for $V_{01}$ (which, for these parallel-series shocks, is equivalent to $V_0$).

Since the total stored energy in capacitors $C_A$ and $C_B$ is given by:

$$E_{stored} = \frac{1}{2}(C_A + C_B) \cdot V_0^2 \quad \text{(Eq. 14)}$$

then the optimal relationship between $C_A$ and $C_B$ that maximizes myocardial voltage for a given total stored energy can be found by substituting $C_A = k \cdot C_B$ into Equation (14) and then solving for $k$ in $\partial E_{stored}/\partial k = 0$. The result is:

$$k^{opt} = C_A/C_B = 1 \quad \text{(Eq. 15)}$$

The above result implies that $C_A$ should equal $C_B$ in order to achieve maximum myocardial impact for any given total energy. The relationship $C_A = C_B$ is equivalent to $\tau_{s1} = 4\tau_{s2}$ [see Equation (9)], from which simplified versions of Equations (11)–(13) can be derived:

$$d_1^{opt} = -\frac{\tau_m}{\alpha_1} \cdot \ln\left\{\left(\frac{1}{3}\right)\left(1 + \frac{\tau_m}{2\tau_{s2}}\right)\right\} \quad \text{(Eq. 16)}$$

$$d_2^{opt} = +\frac{\tau_m}{\alpha_2} \cdot \ln\left\{\left(\frac{1}{3}\right)\left(1 + \frac{2\tau_{s2}}{\tau_m}\right)\right\} \quad \text{(Eq. 17)}$$

$$V_{m2}(d_1^{opt}, d_2^{opt}) = 2V_{01}\left(\frac{\tau_m}{2\tau_{s2}}\right)^{\frac{1}{\alpha_2}-1}\left[\left(\frac{1}{3}\right)\left(1 + \frac{\tau_m}{2\tau_{s2}}\right)\right]^{\frac{1}{\alpha_1}-\frac{1}{\alpha_2}} \quad \text{(Eq. 18)}$$

Finally, the optimal capacitance for a given $R_s$ and $\tau_m$ is determined by finding the value of $C_A$ that minimizes $E_{stored}$, that is, solving for $C_A$ in $\partial E_{stored}/\partial C_A = 0$ (with k=1). The result is:

$$C_A = C_B = \frac{\tau_m}{R_s} \quad \text{(Eq. 19)}$$

or equivalently, the optimal capacitance (for a given $R_s$ and $\tau_m$) is that which satisfies:

$$\tfrac{1}{2}\tau_{s1} = 2\tau_{s2} = \tau m \quad \text{(Eq. 20)}$$

Under these ideal conditions, the optimal step durations are:

$$d_1^{opt} = +2\tau_m \cdot \ln[3/2] \approx 0.811 \cdot \tau_m \quad \text{(Eq. 21)}$$

$$d_2^{opt} = +\tau_m \cdot \ln[/2] \approx 0.405 \cdot \tau_m \quad \text{(Eq. 22)}$$

Figure 12:
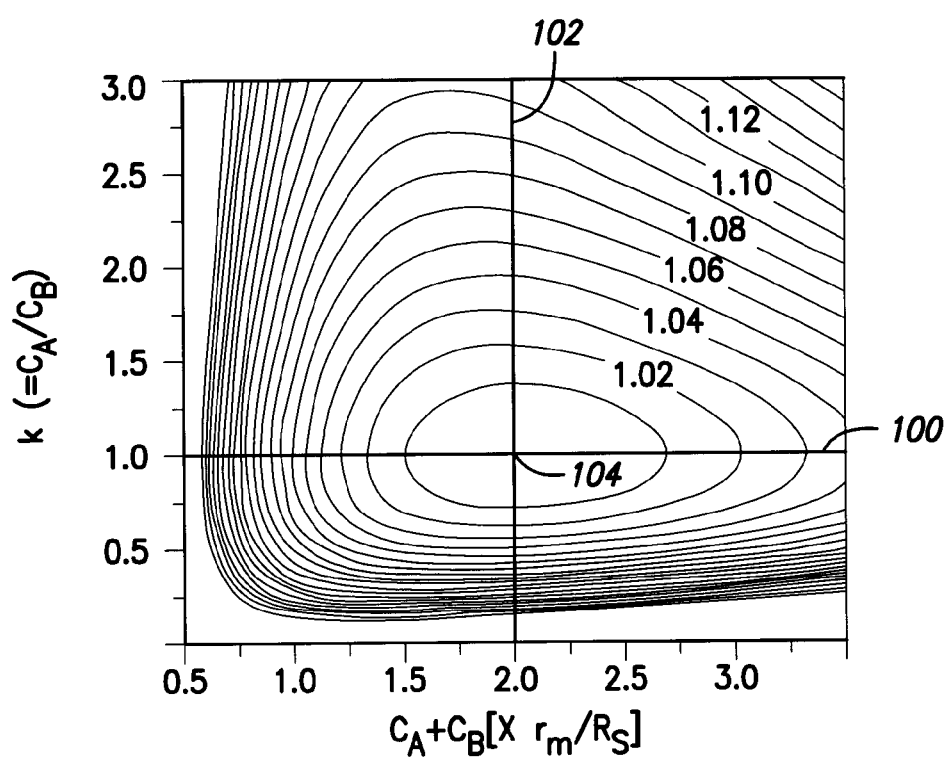
FIG. 12 shows a first contour plot of stored energy as a function of a scaling factor "K" (equivalent to $C_A/C_B$ and the total capacitance ($C_A/C_B$ as scaled by $\tau_m/R_S$)

Further insights into the preceding theoretical calculations can be gleaned from corresponding graphical analyses. The relative stored energy required for defibrillation ($E_{stored}$) for all possible parallel-series two-step waveforms is graphically illustrated in the contour plot of FIG. 12. In this plot, the x-axis is indexed by the total capacitance ($C_A + C_B$, scaled by $\tau_m/R_s$) while the y-axis is indexed by the ratio of the two capacitances ($k = C_A/C_B$,). Although perhaps seemingly non-intuitive axis definitions, they efficiently provide complete coverage of the entire parameter space of all possible capacitor combinations for two-step waveforms. As indicated by the horizontal line 100 and the vertical line 102 overlaid on this plot (and as consistent with the conclusions of Equations (15) and (19)), the most efficient two-step positive portion for the biphasic shock is delivered when:

k=1.0; and $C_A + C_B = 2 \cdot \tau_m/R_s$;

which occurs at point 104 in FIG. 12.

The contours then step out from this optimal point in 1% increments, thus providing an indication as to the relative sensitivity of the energy efficiency to deviations in either total capacitance or capacitance ratio. In fact, energy efficiency remains quite robust: for example, energy efficiency remains within 1% of optimal for:

$\sim 1.5 \cdot \tau_m/R_s < (C_A + C_B) < \sim 2.7 \cdot \tau_m/R_s$;

and $\sim 0.7 < k < \sim 1.4$.

Figure 13:
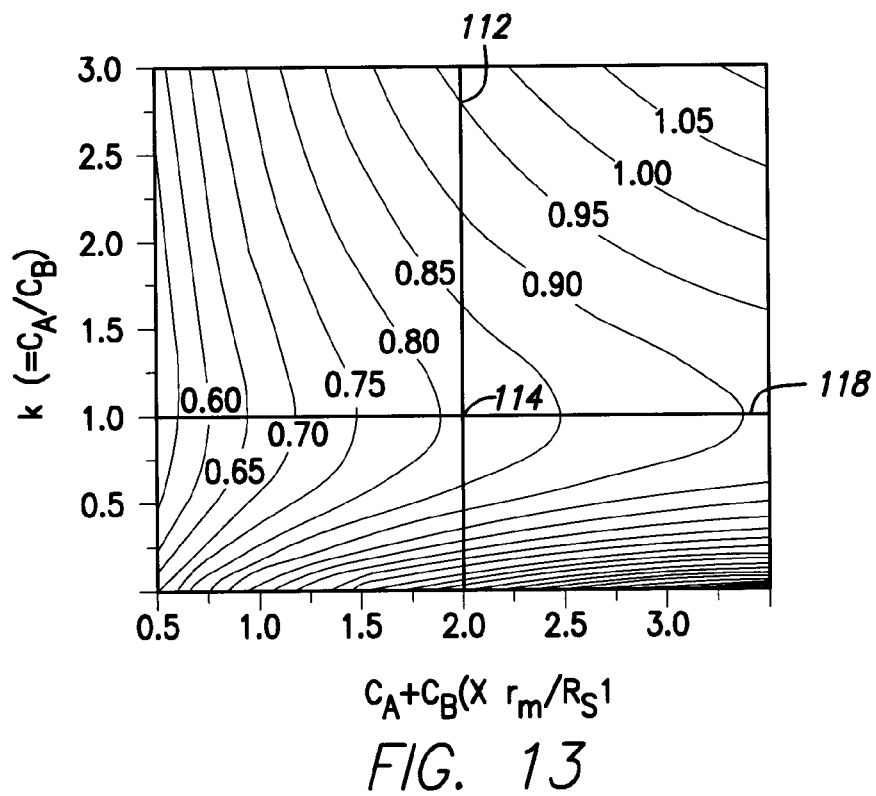
FIGS. 13 and 14 show a second and third contour plot of the $d_1$ and $d_2$, respectively, as a function of the scaling factor K and the total capacitance, wherein the optimal value occurs at the cross-hair.
Figure 14:
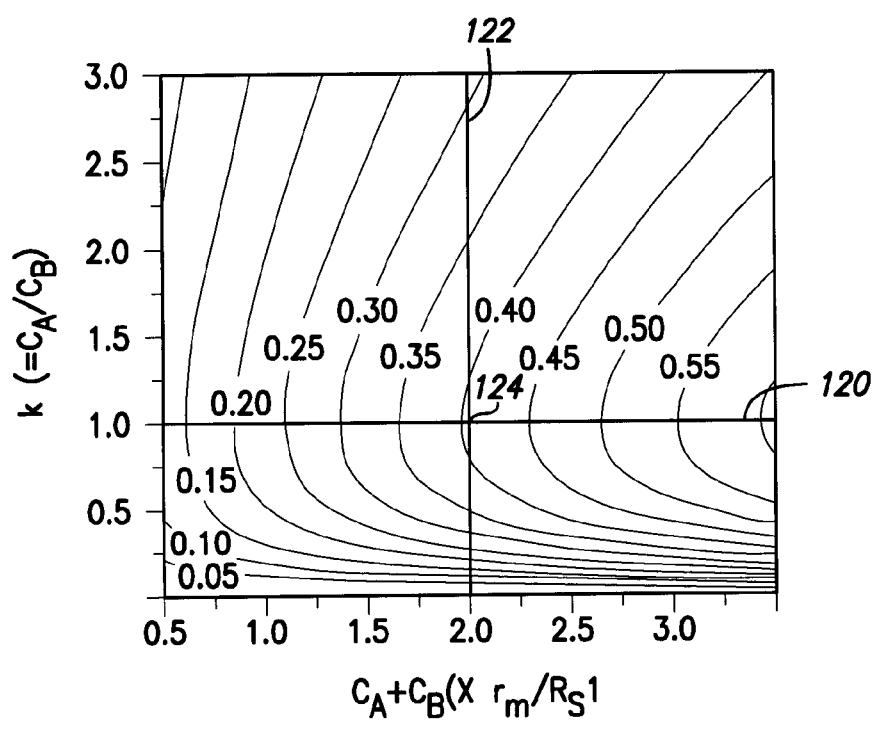

Two-dimensional contour plots of optimal Step1 and Step2 durations (normalized by $\tau_m$, i.e., $d_1^{opt}/\tau_m$ and $d_2^{opt}/\tau_m$) as given by Equations (11) and (12) are presented in FIGS. 13 and 14, respectively.

Similar to FIG. 12, FIGS. 13 and 14 have respective horizontal lines 110, 120 and vertical lines 112, 122 from have been overlaid on these contour maps as well. Their respective intersections 114, 124 appropriately correspond to the "0.811" and "0.405" coefficients found in Equations (21) and (22), respectively.

Since $R_s$ and $\tau_m$ represent patient-specific variables that directly impact the choice of durations used for these stepped waveforms, it is perhaps useful to present example values for $d_1^{opt}$ and $d_2^{opt}$ for a representative range of values for $R_s$ (30–90Ω), $\tau_m$ (2–4 ms), and $C_A$ (30–90 μF). The tables shown in FIGS. 15–17 provide such a set of example values, wherein values for $d_1^{opt}$ and $d_2^{opt}$ are computed from Equations (16) and (17), respectively.

Given the limits of the ranges used for $R_s$, $\tau_m$, and $C_A$ in the tables shown in FIGS. 15–17, $d_1^{opt}$ and $d_2^{opt}$ range from lows of 1.286 and 0.422 ms (when $\tau_m=2$ ms, $C_A=30$ μF, and $R_s=30Ω$ to highs of 3.704 and 2.689 ms (when $\tau_m=4$ ms, $C_A=90$ μF, and $R_s=90Ω$), respectively.

To summarize the above, for the ranges of:

τm=2–4 ms;

$R_s$=30–90Ω;

$C_A=C_B$=30–90 μF

Then, the optimum durations fall in the ranges:

$d_1^{opt}$=1.286–3.704

$d_2^{opt}$=0.422–2.689

Of course, $d_1^{opt}$ and/or $d_2^{opt}$ could move outside of these ranges if any one or more of $R_s$, $\tau_m$, and $C_A$ exceed the limits used for these tables. In those cases, Equations (16) and (17) could be used to compute exactly the optimal step durations for any combination of $R_s$, $\tau_m$, and $C_A$.

In another embodiment, the device could also determine $d_1^{opt}$ and $d_2^{opt}$ based on measured values for $R_s$, and/or a programmed value for $\tau_m$, based on a particular value for $C_A$ and $C_B$.

By way of example, if the capacitance value for $C_A$ and $C_B$ is set to 60 μF, so that Equation 19 is satisfied for a tissue resistance, $R_s$, equal to nominally 50 ohms and a tissue time constant, $\tau_m$, then for a range for $\tau_m$, of 2 ms to 4 ms, and a range for $R_s$ of 30–90 ohms, then:

If $\tau_m$=2.0 ms and Rs=90 ohms, then:
$(C_A+C_B)*R_s/\tau m=5.4$
$d_1^{opt}=0.962*\tau_m(=1.923$ ms$)$
$d_2^{opt}=0.809*\tau_m(=1.618$ ms$)$ If $\tau_m$=4.0 ms and Rs=30 ohms, then:
$(C_A+C_B)*R_s/\tau_m=0.9$
$d_1^{opt}=0.643*\tau_m$ (=2.573 ms)
$d_2^{opt}=0.211*\tau_m$ (=0.844 ms)

Figure 18:
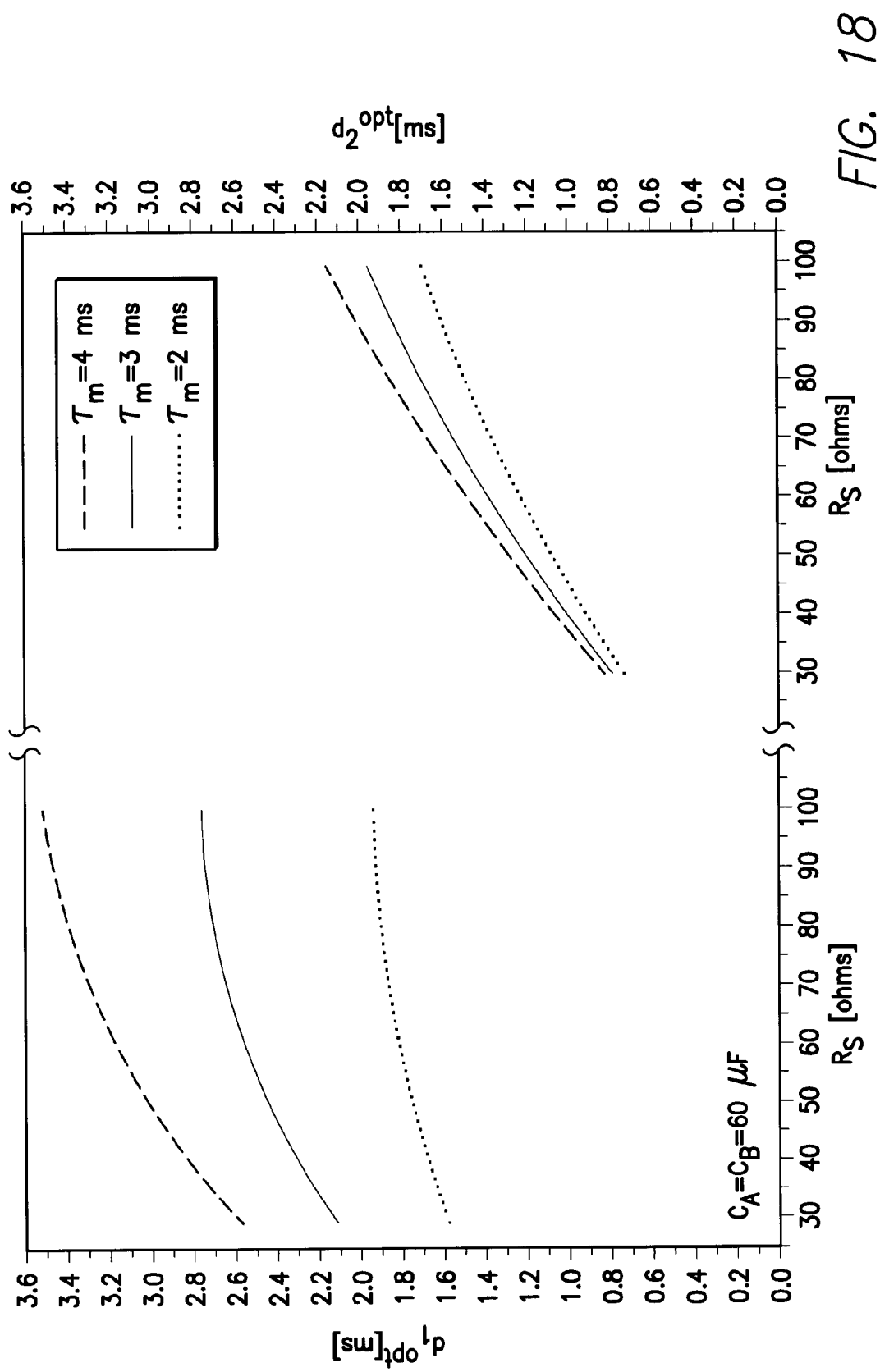
FIG. 18 is a graph of optimal durations for $d_1$ and $d_2$ as a function of tissue resistance ($R_s$) for desired (e.g., 60 $\mu$F) capacitor and a range of tissue time constants ($\tau_m$)

To further assist with interpreting the results embodied in FIGS. 13 and 14 and the table shown in FIGS. 15–17, FIG. 18 graphs a subset of those data as simple functions of $R_s$ and $\tau_m$. In particular, FIG. 18 presents a pair of graphs: the left and right halves plot $d_1^{opt}$ and $d_2^{opt}$, respectively, as functions of $R_s$ for three representative values of $\tau_m$ (2, 3, and 4 ms). For these graphs, $C_A=C_B=60$ μF (thus k=1.0). Consistent with the data in the tables shown in FIGS. 15–17 both $d_1^{opt}$ and $d_2^{opt}$ increase in value with increasing $R_s$ or $\tau_m$. Moreover, this figure helps illustrate how $d_1^{opt}$ appears significantly more sensitive to relative changes in $\tau_m$ than in $R_s$, while $d_2^{opt}$ appears to have the opposite sensitivity.

While FIGS. 12–17 provide a comprehensive overview of all possible parallel-series two-step waveforms, it is also useful to consider some specific examples that can aid in illustrating the relative improvements gained by using such a parallel-series two-step capacitor arrangement over the traditional one-step arrangement.

Figure 19:
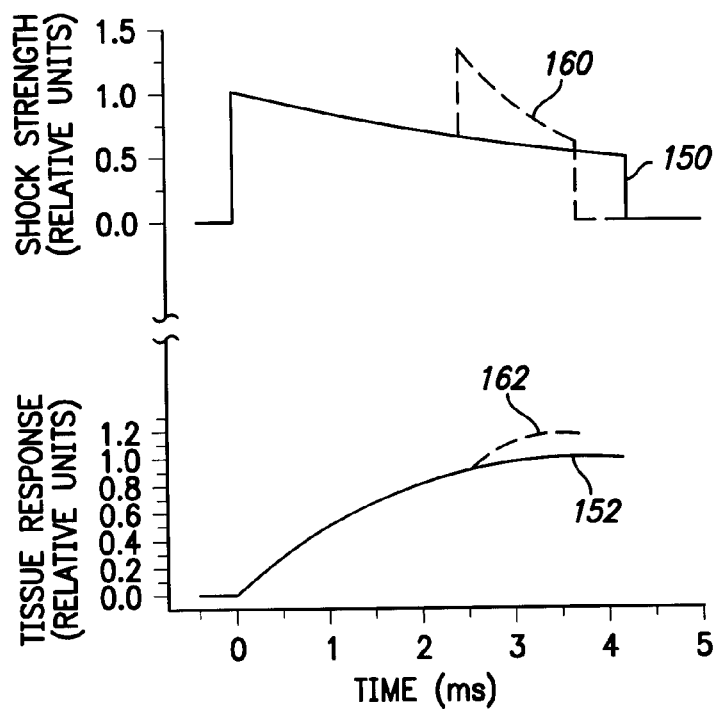
FIG. 19 illustrates a single-step and a two-step (parallel/series) waveform of equal stored energy and their resulting cell membrane responses.

FIG. 19 graphically compares the positive portion of the biphasic shock waveform shapes ($V_s$, top two waveforms, 150 and 160) and associated tissue responses ($V_m$, bottom two waveforms, 152 and 162) for one-step, 150, and parallel-series two-step, 160, shocks having equal stored energies and leading-edge voltages.

For this example, shown in FIG. 19:

$\tau_m$=3 ms, $R_s$=50Ω, $C_A=C_B$=60 μF (thus, Equations 15 & 19 are satisfied).

The one-step shock is generated by essentially keeping $C_A$ and $C_B$ in a parallel arrangement for its entire shock duration, for a constant effective capacitance of 120 μF. As is evident from the tissue responses (i.e., comparing the one-step response 152 to the two-step response 162), two-step the myocardial voltage (162) reaches a higher final cell membrane potential (+18.6%) in a shorter total duration (3.65 vs. 4.16 ms ⇒–12.3%) as compared to the final cell membrane potential (152) using the one-step shock. A consequence of this improved tissue response is that this two-step waveform requires a lower effective leading-edge voltage (and hence a lower stored energy) to achieve the same defibrillation efficacy as its equivalent one-step waveform.

Figure 20:
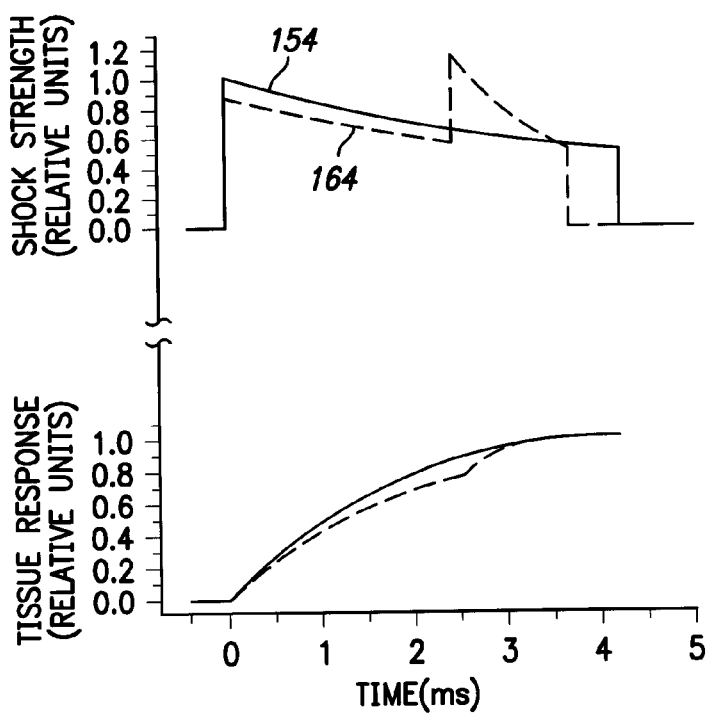
FIG. 20 illustrates the single-step and the two-step waveforms normalized to achieve the maximum cell member response.

FIG. 20 illustrates this scenario by resealing the results presented in FIG. 19 such that the strength of each shock is sufficient to produce tissue responses of equal amplitudes. Consistent with the results presented in FIG. 19, this two-step positive portion of the biphasic shock waveform 164 theoretically requires a 15.6% lower leading-edge voltage than its one-step counterpart 154, which translates into a 28.8% reduction in required stored energy, and a potentially lower pain waveform for the patient since the leading edge of the shocking pulse is reduced.

Figure 21:
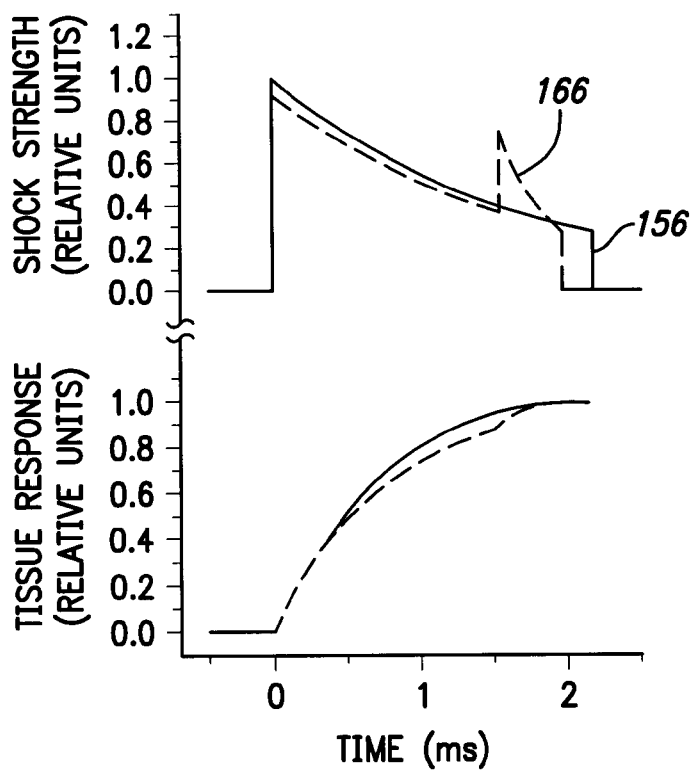
FIGS. 21 and 22 illustrate analogous results to those depicted in FIG. 20 albeit for extreme combinations of $R_s$ and $C_A$ (=$C_B$)
Figure 22:
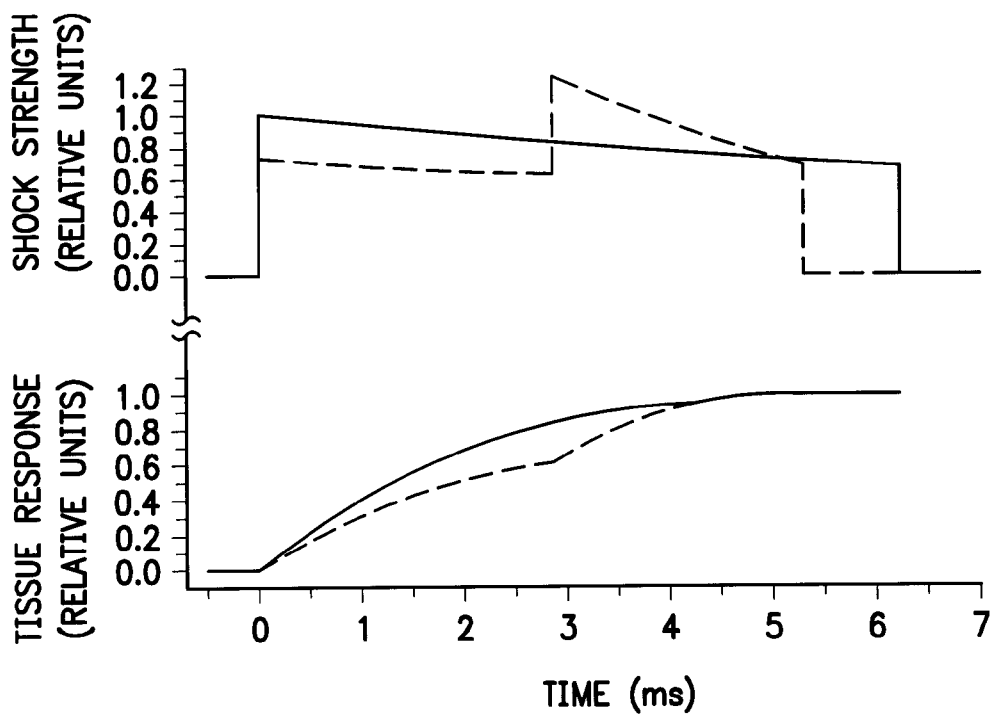

FIGS. 21 and 22 illustrate analogous results to those depicted in FIG. 20, but for relatively extreme combinations of $R_s$ and $C_A$. In FIG. 21, $R_s$=30Ω and $C_A=C_B$=30 μF, while in FIG. 22, $R_s$=90Ω and $C_A=C_B$=90 μF. As is evident in FIGS. 21 and 22, the shape of the optimal parallel-series two-step waveform depends strongly on the magnitudes of $R_s$ and $C_A$. Furthermore, the relative improvement in energy efficiency also strongly depends on these values.

For example, in FIG. 21, the two-step waveform 166 induced an equivalent final tissue response as its one-step waveform 156, but with an 8.8% shorter duration (2.1 vs. 2.3 ms), a 6.5% lower leading-edge voltage, and a 12.6% reduction in required stored energy.

In FIG. 22, the relative improvements were a 14.3% shorter duration (5.3 vs. 6.3 ms), a 25.9% lower leading-edge voltage, and a 45.0% reduction in required stored energy. Thus, these comparisons suggest that there would be especially great incentive for utilizing two-step waveforms instead of traditional one-step waveforms when the magnitudes of $R_s$ and $C_A$ are large, while the incentive is relatively minimal when the magnitudes of $R_s$ and $C_A$ are small. Unfortunately, because of the inherent limitations of this theoretical model, it is not possible to directly compare amplitude-based results (e.g., leading-edge voltage, required stored energy) derived for differing $R_s$ or $\tau_m$. For this reason, the results of FIGS. 20–22 are all self-normalized (that is, there is no relationship between the amplitudes in these graphs).

Finally, while Equations (16) and (17) provide exact formulas for determining $d_1^{opt}$ and $d_2^{opt}$ when k=1 (i.e., $C_A=C_B$), it is sometimes helpful and/or practical to also identify various approximations to such solutions. Consider the following infinite series expansion of the natural logarithm:

$$\ln[x] = 2 \cdot \left[\left(\frac{x-1}{x+1}\right) + \frac{1}{3} \cdot \left(\frac{x-1}{x+1}\right)^3 + \frac{1}{5} \cdot \left(\frac{x-1}{x+1}\right)^5 + \ldots\right] \quad (x > 0) \quad \text{(Eq. 23)}$$

Utilizing just the first term of this expansion, Equations (16) and (17) can be simplified to:

$$d_1^{opt} \approx \frac{2\tau_m}{3-\alpha_1} = \frac{2\tau_{s1} \cdot \tau_m}{2\tau_{s1} + \tau_m} \Rightarrow \quad \text{(Eq. 24)}$$

$$\frac{1}{d_1^{opt}} \approx \frac{1}{2\tau_{s1}} + \frac{1}{\tau_m} = \frac{1}{4R_sC_A} + \frac{1}{\tau_m}$$

$$d_2^{opt} \approx \frac{2\tau_m}{3-2\alpha_2} = \frac{\tau_{s2} \cdot 2\tau_m}{\tau_{s2} + 2\tau_m} \Rightarrow$$

$$\frac{1}{d_2^{opt}} \approx \frac{1}{\tau_{s2}} + \frac{1}{2\tau_m} = \frac{1}{2} \cdot \left(\frac{4}{R_s C_A} + \frac{1}{\tau_m}\right) \quad \text{(Eq. 25)}$$

In words, these relationships suggest that the optimal step durations can be well approximated by computing variously weighted parallel combinations of system and myocardial time constants. And despite using only one term of Equation (23), these approximations are relatively quite accurate over a broad range of $\tau_{s1}/\tau_m$ and $\tau_{s2}/\tau_m$ ratios (only their ratios, not their absolute values, impact their accuracy). For example, the relative error for $d_1^{opt}$ is less than 5% for $0.4 < \tau_{s1}/\tau_m < 5$, while the relative error for $d_1^{opt}$ is less than 5% for $0.2 < \tau_{s2}/\tau_m < 3$. When Equation (20) is also satisfied (that is, when system and myocardial time constants are ideally matched), these relative errors are each only 1.35%. In all cases, these approximation calculations underestimate the true values by these respective relative errors.

Optimal Three-Step Positive Phase Pulse Generation

Figure 23:
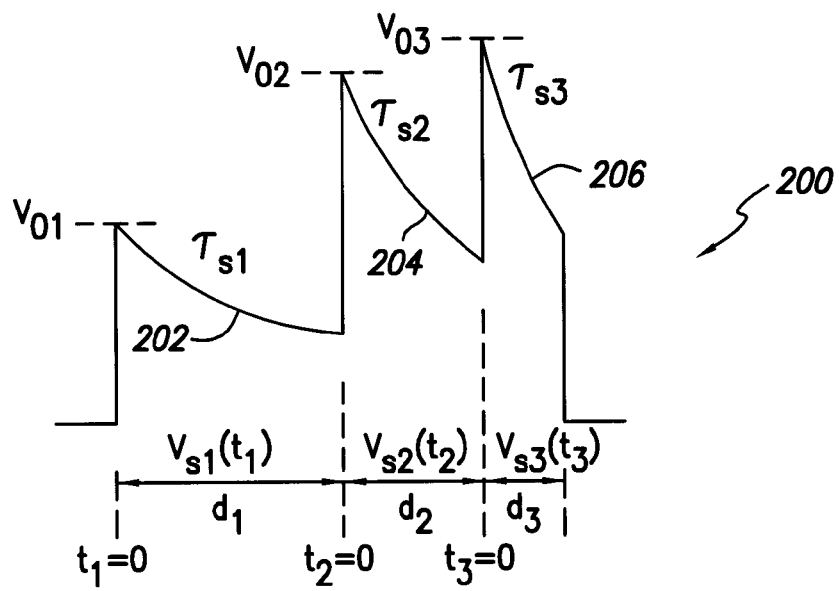
FIG. 23 illustrates the general shape of a three-step defibrillation waveform that may be generated using the three-capacitor ICD of FIG. 4.

In the forgoing, techniques for generating two- and three-step biphasic shocking pulses have been described wherein the first (typically positive) phase of the biphasic pulse has no more than two voltage peaks. In the following, techniques will be described for generating a biphasic shocking pulse wherein the positive phase of the pulse has three distinct voltage peaks. Pulse 200, illustrated in FIG. 23, is generated using the three-capacitor circuit of FIG. 4, but controlled so as to generate a biphasic pulse having a positive phase containing three distinct voltage peaks. (In FIG. 23, only the positive phase of the biphasic pulse is shown.) The three capacitors are discharged as follows: a first step or portion 202 of the pulse waveform is generated by discharging capacitors C1, C2, and C3 while all three are connected in parallel for a time period of $d_1$; a second step 204 of the pulse waveform is generated by discharging the capacitors while the C1 and C2 are connected in parallel and C3 is connected in series for a time period of $d_2$; and a third step 206 of the pulse waveform by discharging the capacitors while all three are connected in series for a time period of $d_3$. The duration of each phase is selected to maximize the final myocardial voltage within the heart tissue receiving the pulse. To this end, the initial voltage of each capacitor is set to $V_0$ and the optimal time durations for each phase of the pulse are as follows:

$$d_1^{opt} = -\frac{\tau_m}{\alpha_1} \cdot \ln\left\{\left(\frac{\tau_m}{\tau_{s1}}\right)\left(\frac{2 - \frac{\alpha_2}{\alpha_1}}{1 - \frac{\alpha_2}{\alpha_1}}\right)\right\}; \quad \text{(Eq. 26)}$$

$$d_2^{opt} = +\frac{\tau_m}{\alpha_2} \cdot \ln\left\{\left(\frac{1}{2}\right)\left(\frac{2 - \frac{\alpha_2}{\alpha_1}}{1 - \frac{\alpha_2}{\alpha_1}}\right)\left(\frac{1 - \frac{\alpha_3}{\alpha_2}}{K_C - \frac{\alpha_3}{\alpha_2}}\right)\right\}; \text{ and} \quad \text{(Eq. 27)}$$

$$d_3^{opt} = -\frac{\tau_m}{\alpha_3} \cdot \ln\left\{(K_C)\left(\frac{1 - \frac{\alpha_3}{\alpha_2}}{K_C - \frac{\alpha_3}{\alpha_2}}\right)\right\} \quad \text{(Eq. 28)}$$

In the Equations (26)–(28), $$K_C = 1 + (C_C)/(C_A + C_B + C_C); \quad \text{(Eq. 29)}$$

$$\alpha_1 = (\tau_m/\tau_{s1}), \alpha_2 = 1 - (\tau_m/\tau_{s2}), \text{ and } \alpha_3 = 1 - (\tau_m/\tau_{s3}); \quad \text{(Eq. 30)}$$

$$\tau_{s1} = R_s \cdot C_{s1}, \tau_{s2} = R_s \cdot C_{s2}, \text{ and } \tau_{s3} = R_s \cdot C_{s3}; \quad \text{(Eq. 31)}$$

$$C_{s1} = C_A + C_B + C_C; \quad \text{(Eq. 32)}$$

$$C_{s2} [(C_A + C_B) \cdot (C_C)] / [C_A + C_B + C_C]; \quad \text{(Eq. 33)}$$

$$C_{s3} = 1 / \left[\frac{1}{C_A} + \frac{1}{C_B} + \frac{1}{C_C}\right] \quad \text{(Eq. 34)}$$

$C_A$, $C_B$, & $C_C$ are the capacitances, respectively, of the first, second and third capacitors C1, C2 and C3; and $\tau_m$ is a predetermined myocardial tissue time constant.

Note that $C_A$, $C_B$, & $C_C$ are the capacitances of the capacitors C1, C2 and C3 of the three capacitor system of FIG. 4 and should not be confused with the capacitances of capacitors $C_A$, $C_B$ of the two capacitor system of FIG. 3. To clarify, all references herein to $C_A$, $C_B$, & $C_C$ within the equations of the Summary, the Claims, FIGS. 23 and following and Equations 26 and following refer to the capacitances of the capacitors C1, C2 and C3 of the three capacitor system of FIG. 4.

Preferably, the capacitances of the three capacitors are selected so as to minimize the amount of required stored energy while achieving the maximum final myocardial voltage. To minimize the amount of required stored energy, the capacitances are set to:

$$C_A^{opt} = 0.6673 \cdot \left(\frac{\tau_m}{R_s}\right); \quad \text{(Eq. 35)}$$

$$C_B^{opt} = 0.6673 \cdot \left(\frac{\tau_m}{R_s}\right); \text{ and} \quad \text{(Eq. 36)}$$

$$C_C^{opt} = 1.5356 \cdot \left(\frac{\tau_m}{R_s}\right); \text{ wherein} \quad \text{(Eq. 37)}$$

$R_s$ is a predetermined system resistance.

By using the optimal capacitance values, the optimal discharge time periods $d_1^{opt}$, $d_2^{opt}$, and $d_3^{opt}$ for use in maximizing the myocardial potential may be simplified to:

$$d_1^{opt} = 0.878 \cdot \tau_m; \quad \text{(Eq. 38)}$$

$$d_2^{opt} = 0.277 \cdot \tau_m; \text{and} \quad \text{(Eq. 39)}$$

$$d_3^{opt} = 0.200 \cdot \tau_m \quad \text{(Eq. 40)}$$

Figure 24:
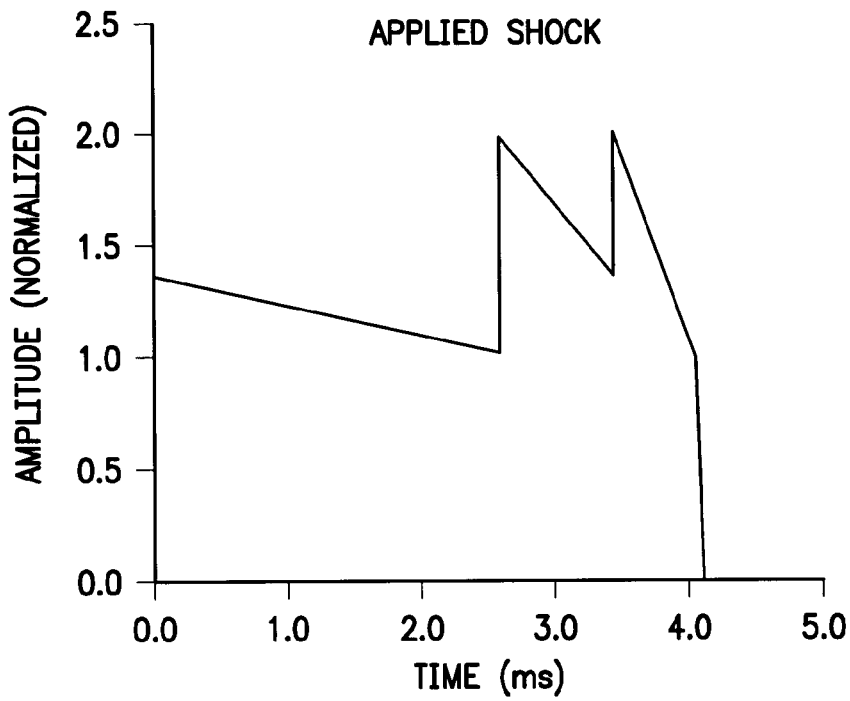
FIG. 24 illustrates a specific exemplary defibrillation waveform having a three-step positive generated using the three-capacitor ICD of FIG. 4.
Figure 25:
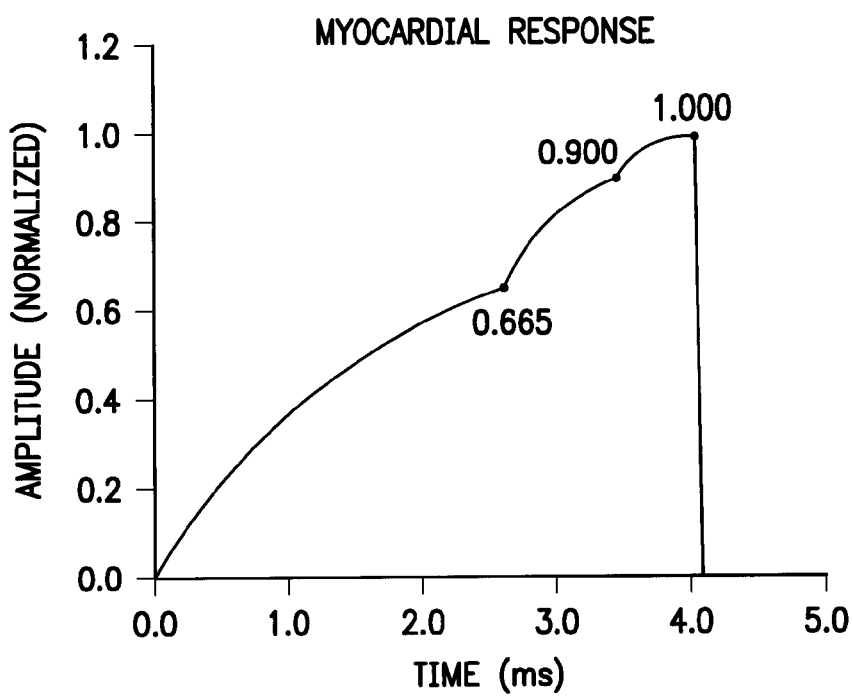
FIG. 25 depicts the excitable cardiac membrane response during the defibrillation waveform of FIG. 24.

FIG. 24 depicts the positive phase of an exemplary defibrillation waveform generated by this technique when using a specific set of exemplary parameters (specified in the following three tables). FIG. 25 depicts an exemplary excitable cardiac membrane response evoked by the defibrillation waveform of FIG. 24.

TABLE I

| Description | Var | Value | Optimal | Units |
|---|---|---|---|---|
| System resistance | Rs | 50.0 | | ohms |
| Myocardial time constant | $\tau_\mu$ | 3.00 | | ms |
| Capacitor A | CA | 40.0 | 40.0 | $\mu\Phi$ |
| Capacitor B | CB | 40.0 | 40.0 | $\mu\Phi$ |
| Capacitor C | CC | 92.1 | 92.1 | $\mu\Phi$ |
| Total Capacitance | Ctotal | 172.2 | 172.2 | $\mu\Phi$ |

TABLE II

Derived Intermediate Values

| Description | Var | Value | Units |
|---|---|---|---|
| Step 1 time constant | $\tau\sigma 1$ | 8.61 | ms |
| Step 2 time constant | $\tau\sigma 2$ | 2.14 | ms |
| Step 3 time constant | $\tau\sigma 3$ | 0.82 | ms |
| alpha 1 | $\alpha 1$ | 0.65 | none |
| alpha 2 | $\alpha 2$ | −0.40 | none |
| alpha 3 | $\alpha 3$ | −2.65 | none |

TABLE III

Optimal Values

| Description | Var | Value | Units |  |
|---|---|---|---|---|
| Optimal Step 1 duration | d1 | 2.64 | ms | |
| Optimal Step 2 duration | d2 | 0.83 | ms | |
| Optimal Step 3 duration | d3 | 0.60 | ms | |
| Total duration | dtotal | 4.07 | ms | |
| Step 1 leading-edge voltage | V01 | 1.00 | 1.35 | |
| Step 2 leading-edge voltage | V02 | 1.47 | 1.99 | |
| Step 3 leading-edge voltage | V03 | 1.53 | 2.07 | (rel units) |
| Step 1 myo. final voltage | Vm1f | 0.49 | 0.67 | |
| Step 2 myo. final voltage | Vm2f | 0.67 | 0.90 | |
| Step 3 myo. final voltage | Vm3f | 0.74 | 1.00 | (rel units) |

By configuring and operating the three capacitor shocking circuit as just summarized, the amount of energy required to reach a myocardial defibrillation threshold is less than for one-capacitor or two-capacitor systems, regardless of the total capacitance of the system. Hence, power can be saved, while still providing effective defibrillation. Moreover, the total time required to reach the myocardial defibrillation threshold is less than with one-capacitor or two-capacitor systems, permitting the patient to be defibrillated more quickly. Additionally, using the three capacitor system to generate pulses having a three-step positive phase is generally less influenced by variations in underlying parameters and operating conditions, than one- or two-capacitor arrangements.

In view of the foregoing, a method for making and using an ICD exploiting an optimal three-step positive-phase shocking pulse may be exploited. The method is summarized in FIG. 26. Initially, at step 250, the system resistance $R_s$ (as seen by the shocking circuit) and the myocardial tissue time constant $\tau_m$ are determined by conventional techniques. Then, at step 252, the optimal capacitance values for the three capacitors are determined using Equations (35)–(37). At step 254, the optimal discharge time values for the three phases of the pulse waveform are determined using Equations (38)–(40). An ICD is then fabricated, at step 256, with shocking circuit capacitors having the optimal capacitances and programmed to discharge the capacitors for the optimal time periods. The ICD is then implanted within a patient at step 258 and is activated to detect ventricular fibrillation. The capacitors are charged to a selected voltage. Upon detection of fibrillation, at step 260, the ICD discharges the capacitors using the sequence described above to deliver a three-step positive phase of the shocking pulse to the patient for terminating fibrillation. If the first pulse fails to terminate fibrillation, additional pulses may be delivered, perhaps using higher voltage levels. Note that, if it is not practicable to provide an ICD with capacitors exactly matching the optimal capacitance values, approximate values may be employed instead. If so, then values for the discharge time periods are calculated for use with the actual capacitance values using Equations (26)–(28), and the ICD is programmed accordingly.

Table IV provides a summary of the parameters for the three distinct steps of the waveform:

TABLE IV

| | | |
|---|---|---|
| Step1 | Capacitor Arrangement | $C_A$, $C_B$, and $C_C$ in parallel |
| | Effective Capacitance | $C_{s1} = C_A + C_B + C_C$ |
| | Decay Time Constant | $\tau_{s1} = R_s \cdot C_{s1}$ |
| | Leading Edge Voltage | $V_{01} = V_0$ |
| | Total Voltage Profile | $V_{s1}(t_1) = V_{01} \cdot \exp[-t_1/\tau_{s1}]$  $0 \leq t_1 \leq d_1$ |
| Step2 | Capacitor Arrangement | $C_A$ and $C_B$ in parallel, $C_C$ in series |
| | Effective Capacitance | $C_{s2} = [(C_A + C_B) \cdot (C_C)]/[C_A + C_B + C_C]$ |
| | Decay Time Constant | $\tau_{s2} = R_s \cdot C_{s2}$ |
| | Leading Edge Voltage | $V_{02} = 2 \cdot V_{s1}(d_1)$ $= 2 \cdot V_0 \cdot \exp[-d_1/\tau_{s1}]$ |
| | Total Voltage Profile | $V_{s2}(t_2) = V_{02} \cdot \exp[-t_2/\tau_{s2}]$  $0 \leq t_2 \leq d_2$ |
| Step3 | Capacitor Arrangement | $C_A$, $C_B$, and $C_C$ in series |
| | Effective Capacitance | $C_{s3} = 1 / \left[ \dfrac{1}{C_A} + \dfrac{1}{C_B} + \dfrac{1}{C_C} \right]$ |
| | Decay Time Constant | $\tau_{s3} = R_s \cdot C_{s3}$ |
| | Leading Edge Voltage | $V_{03} = K_C \cdot V_{s2}(d_2)$ $= 2 \cdot K_C \cdot V_0 \cdot \exp[-d_1/\tau_{s1}] \cdot \exp[-d_2/\tau_{s2}]$ where $K_C = 1 + \dfrac{C_C}{C_A + C_B + C_C}$ |
| | Total Voltage Profile | $V_{s3}(t_3) = V_{03} \cdot \exp[-t_3/\tau_{s3}]$ $0 \leq t_3 \leq d_3$ |

The aforementioned optimal pulse phase durations and capacitance values have been derived as follows. The defibrillation waveform is represented by:

$$V_{s1}(t_1) = V_{01} \cdot \exp[-t_1/\tau_{s1}] \quad 0 \leq t_1 \leq d_1 \qquad \text{(Eq. 41)}$$

$$V_{s2}(t_2) = V_{02} \cdot \exp[-t_2/\tau_{s2}] \quad 0 \leq t_2 \leq d_2 \qquad \text{(Eq. 42)}$$

$$V_{s3}(t_3) = V_{03} \cdot \exp[-t_3/\tau_{s3}] \quad 0 \leq t_3 \leq d_3 \qquad \text{(Eq. 43)}$$

A General Solution for $V_m(t)$ is obtained with the following derivations. Note that the following derivations (Equations (44)–(46)) make no assumptions regarding any specific relationships between the characteristics of Step1, Step2, and Step3.

The idealized myocardial responses ($V_{m1}$, $V_{m2}$, and $V_{m3}$) to the three steps of the applied waveform ($V_{s1}$, $V_{s2}$, and $V_3$) can be described as the solution to the following set of sequential equations:

$$\text{Step1: } \frac{V_{s1}(t_1)}{\tau_m} = \frac{dV_{m1}(t_1)}{dt_1} + \frac{V_{m1}(t_1)}{\tau_m} \qquad \text{(Eq. 44)}$$

$$\text{Step2: } \frac{V_{s2}(t_2)}{\tau_m} = \frac{dV_{m2}(d_1, t_2)}{dt_2} + \frac{V_{m2}(d_1, t_2)}{\tau_m} \qquad \text{(Eq. 45)}$$

$$\text{Step3: } \frac{V_{s3}(t_3)}{\tau_m} = \frac{dV_{m3}(d_1, d_2, t_3)}{dt_3} + \frac{V_{m3}(d_1, d_2, t_3)}{\tau_m} \quad \text{(Eq. 46)}$$

with the corresponding set of initial conditions given as: $V_{m1}(0)=0$, $V_{m2}(d_1,0)=V_{m1}(d_1)$, and $V_{m3}(d_1,d_2,0)=V_{m2}(d_1,d_2)$. The initial conditions specify that the myocardial voltage is initially at a voltage level of zero, and furthermore that the myocardial voltage must be continuous between consecutive steps.

The corresponding general solutions to these differential equations are:

$$\text{Step1: } V_{m1}(t_1) = \frac{V_{01}}{\alpha_1} \cdot \left( \exp\left[\frac{-t_1}{\tau_{s1}}\right] - \exp\left[\frac{-t_1}{\tau_m}\right] \right) \tau_{s1} \neq \tau_m \quad \text{(Eq. 46)}$$

$$\text{Step2: } V_{m2}(d_1, t_2) = \quad \text{(Eq. 47)}$$
$$V_{m1}(d_1) \cdot \exp\left[\frac{-t_2}{\tau_m}\right] + \frac{V_{02}}{\alpha_2} \cdot \left( \exp\left[\frac{-t_2}{\tau_{s2}}\right] - \exp\left[\frac{-t_2}{\tau_m}\right] \right) \tau_{S2} \neq \tau_m$$

$$\text{Step3: } V_{m3}(d_1, d_2, t_3) = \quad \text{(Eq. 48)}$$
$$V_{m2}(d_1, d_2) \cdot \exp\left[\frac{-t_3}{\tau_m}\right] + \frac{V_{03}}{\alpha_3} \cdot \left( \exp\left[\frac{-t_3}{\tau_{s3}}\right] - \exp\left[\frac{-t_3}{\tau_m}\right] \right) \tau_{S3} \neq \tau_m$$

where $\alpha_1=1-(\tau_m/\tau_{s1})$, $\alpha_2=1-(\tau_m/\tau_{s2})$, and $\alpha_3=1-(\tau_m/\tau_m/\tau_{s3})$. (The associated solutions for when $\tau_{s1}=\tau_m$, $\tau_{s2}=\tau_m$, or $\tau_{s3}=\tau_m$ are straightforward, but not relevant to these derivations, and thus are not included here.)

One of the main objectives of these derivations is to find the combination of waveform step durations that will maximize the final myocardial response. This goal corresponds to finding the step durations, $d_1=d_1^{opt}$, $d_2=d_2^{opt}$, and $d_3=d_3^{opt}$, that maximize the final myocardial voltage given by $V_{m3}$ ($t_1=d_1, t_2=d_2, t_3=d_3$). This maximum can be determined by solving for these step durations from the following simultaneous equations:

$$\frac{\partial V_{m3}(d_1^{opt}, d_2^{opt}, d_3^{opt})}{\partial d_1^{opt}} = 0 \quad \text{(Eq. 49)}$$

$$\frac{\partial V_{m3}(d_1^{opt}, d_2^{opt}, d_3^{opt})}{\partial d_2^{opt}} = 0 \quad \text{(Eq. 50)}$$

$$\frac{\partial V_{m3}(d_1^{opt}, d_2^{opt}, d_3^{opt})}{\partial d_3^{opt}} = 0 \quad \text{(Eq. 51)}$$

Given the relationships and definitions presented in the table above, the solutions to this set of equations are:

$$d_1^{opt} = -\frac{\tau_m}{\alpha_1} \cdot \ln\left\{ \left(\frac{\tau_m}{\tau_{s1}}\right) \left( \frac{2 - \frac{\alpha_2}{\alpha_1}}{1 - \frac{\alpha_2}{\alpha_1}} \right) \right\} \quad \text{(Eq. 52)}$$

$$d_2^{opt} = +\frac{\tau_m}{\alpha_2} \cdot \ln\left\{ \left(\frac{1}{2}\right) \left( \frac{2 - \frac{\alpha_2}{\alpha_1}}{1 - \frac{\alpha_2}{\alpha_1}} \right) \left( \frac{1 - \frac{\alpha_3}{\alpha_2}}{K_C - \frac{\alpha_3}{\alpha_2}} \right) \right\} \quad \text{(Eq. 53)}$$

$$d_3^{opt} = -\frac{\tau_m}{\alpha_3} \cdot \ln\left\{ (K_C) \left( \frac{1 - \frac{\alpha_3}{\alpha_2}}{K_C - \frac{\alpha_3}{\alpha_2}} \right) \right\} \quad \text{(Eq. 54)}$$

where $K_C=1+(C_C)/(C_A+C_B+C_C)$.

Note that Equations (52)–(54) define the optimal step durations that maximize final myocardial voltage for any independent values of $C_A$, $C_B$, and $C_C$. However, since efficient use of stored energy is critically important for implantable defibrillators, it is desirable to determine the optimal values for the capacitors that maximizes induced myocardial voltage while minimizing required stored energy. Considering the complexity of the governing equations involved in this optimization problem, finding these capacitor values is best performed numerically using conventional nonlinear optimization techniques. The results are presented in Table V, where the optimal values for the capacitors are defined as functions of the governing ratio $(\tau_m/R_s)$:

TABLE V

| | $C_A^{opt}$ | $C_B^{opt}$ | $C_C^{opt}$ | $C_{total}^{opt}$ |
|---|---|---|---|---|
| Exact Values | $0.6673 \cdot \left(\frac{\tau_m}{R_s}\right)$ | $0.6673 \cdot \left(\frac{\tau_m}{R_s}\right)$ | $1.5356 \cdot \left(\frac{\tau_m}{R_s}\right)$ | $2.8701 \cdot \left(\frac{\tau_m}{R_s}\right)$ |
| Approx Values | $\left(\frac{2}{3}\right) \cdot \left(\frac{\tau_m}{R_s}\right)$ | $\left(\frac{2}{3}\right) \cdot \left(\frac{\tau_m}{R_s}\right)$ | $\left(\frac{3}{2}\right) \cdot \left(\frac{\tau_m}{R_s}\right)$ | $\left(\frac{17}{6}\right) \cdot \left(\frac{\tau_m}{R_s}\right)$ |
| Relative Error | -0.09% | -0.09% | -2.32% | -1.28% |

Thus, for example, with $\tau_m=3$ ms and $R_s=50\Omega$, the optimal values for $C_A$, $C_B$, and $C_C$ are 40.036, 40.036, and 92.136 $\mu$F, respectively, for a total optimal capacitance of 172.208 $\mu$F. For comparison, the capacitance values obtained by using the approximating expressions above are 40, 40, and 90 $\mu$F, respectively, for a total of 170 $\mu$F.

If (and only if) optimal capacitance values (as obtained from the Table above) are utilized as appropriate for the governing system conditions (i.e., the specific values of $\tau_m$ and $R_s$), then Equations (52)–(54) can be simplified dramatically as follows:

$$d_1^{opt}=0.878 \cdot \tau_m \quad \text{(Eq. 55)}$$

$$d_2^{opt}=0.277 \cdot \tau_m \quad \text{(Eq. 56)}$$

$$d_3^{opt}=0.200 \cdot \tau_m \quad \text{(Eq. 57)}$$

Based on the algebraic expressions for optimal capacitance values (as a function of $\tau_m/R_s$) as given in the Table above, the normalized sizes of the capacitors $C_A$, $C_B$, and $C_C$ relative to the total optimal capacitance can be derived as follows:

$$C_A^{opt}/C_{total}^{opt}=C_B^{opt}/C_{total}^{opt}=0.0.2325$$

$$C_C^{opt}/C_{total}^{opt}=0.5350$$

Figure 27:
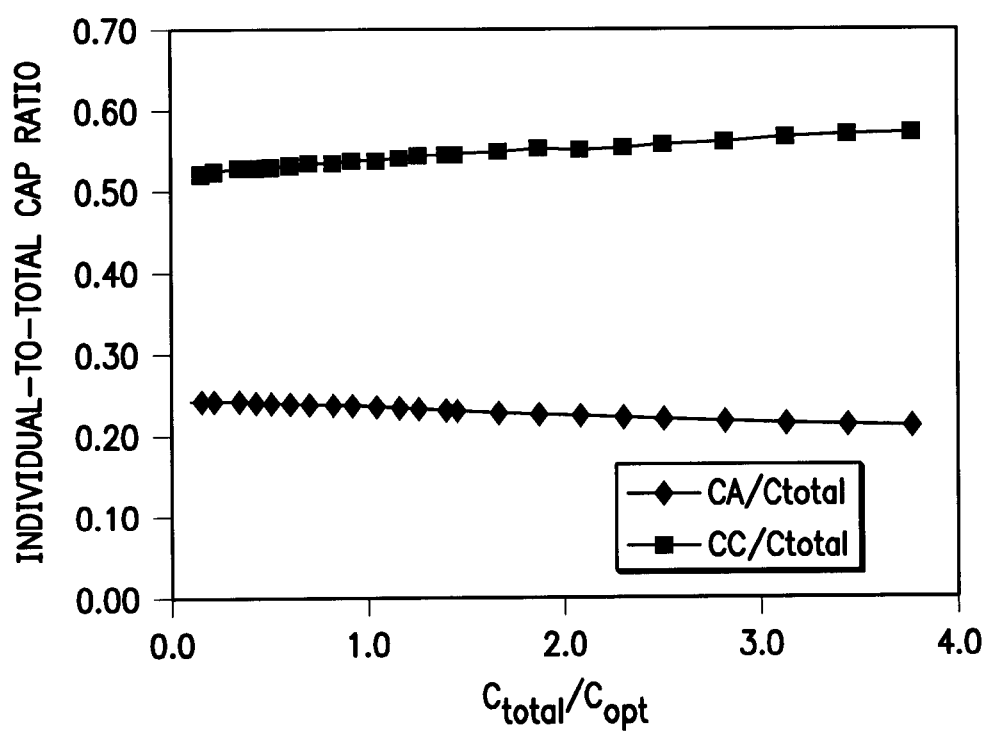
FIG. 27 is a graph the ratio of individual capacitances to total capacitance as a function of the ratio of total capacitance to optimal capacitance for the three-capacitor system used to generate the defibrillation waveform of FIG. 23.

Note that these ratios are not completely invariant to deviations from optimal. That is, the ratios cannot always be employed to calculate the most appropriate individual capacitor values for any given total capacitance (e.g., $C_{total} \neq C_{total}^{opt}$). However, the ratios have been found to be quite usable over a broad range of excursions from optional. As FIG. 27 illustrates, the individual-to-total capacitance ratios do vary slightly as the actual total capacitance diverges from the optimal total capacitance (i.e., $C_{total}/C_{opt} \neq 1$). However, since these ratio variations are relatively insensitive to these excursions (only 0.79% and 1.58% change in $C_A/C_{total}$ and $C_C/C_{total}$, respectively, per unit change in $C_{total}/C_{opt}$), the ratios above are quite satisfactory for most purposes (and can be adjusted by these percentage deviations to provide even further accuracy, if needed).

A comparison of three-capacitor results to those from one-capacitor and two-capacitor systems follows below. Firstly, the results above imply that the total system capacitance for an optimally configured three-capacitor defibrillator is almost $3 \cdot (\tau_m/R_s)$ [the actual coefficient, as indicated in the Table V above, equals 2.8701]. For comparison, the total system capacitance for an optimally configured two-capacitor two-step parallel-series defibrillator (as determined from a previously completed set of derivations) equals exactly $2 \cdot (\tau_m R_s)$, with those two capacitors equal in magnitude. Moreover, the total system capacitance for an optimally configured one-capacitor one-step defibrillator equals only $1 \cdot (\tau_m R_s)$. Thus, the total system capacitance for a three-capacitor defibrillator as recommended from these (idealized) derivations is actually significantly larger than the simpler system designs. However, as will be explained with reference to the remaining figures, the required stored energy is less, the time to defibrillation threshold is faster, and the three-capacitor system is less influenced by underlying parameters and operating conditions.

Figure 28:
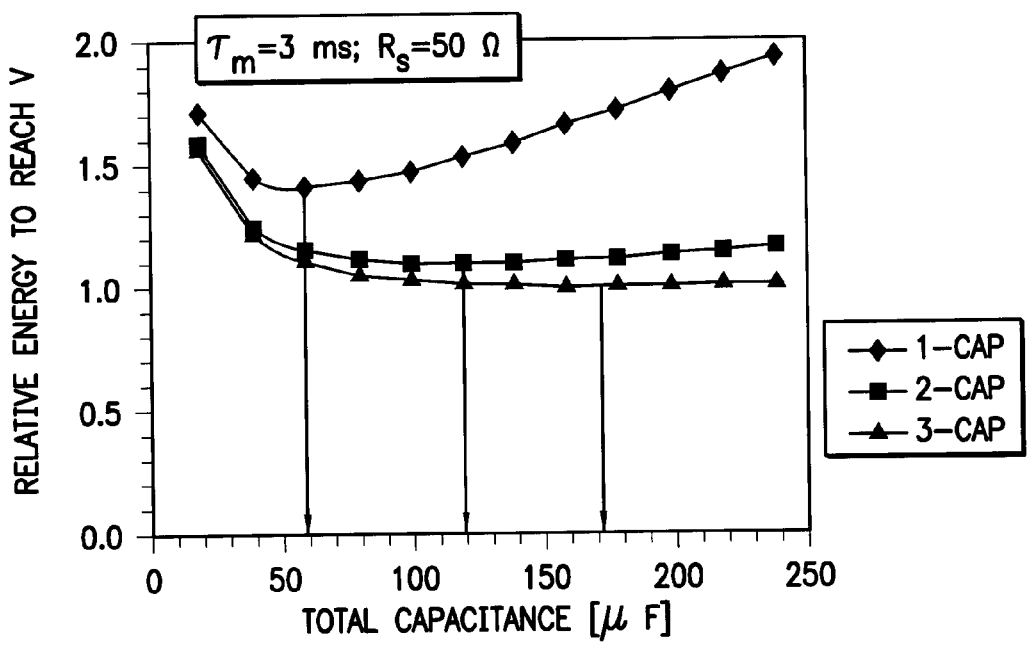
FIG. 28 is a graph the relative energy needed to reach a myocardial defibrillation threshold as a function of total capacitance for one-, two- and three-capacitor shocking circuits showing that the relative energy required is less for the three-capacitor shocking circuit for all values of total capacitance.

FIG. 28 plots the relative total stored energy as a function of total capacitance theoretically required to reach the "defibrillation" threshold ($V_{th}$) for an idealized myocardial tissue model for exemplary one-capacitor, two-capacitor, and three-capacitor systems. In this example, $\tau_m=3$ ms and $R_s=50\Omega$; for other combinations of $\tau_m$ and $R_s$, the quantitative aspects of this plot will change, but the qualitative relationships are not be affected. The drop-arrows superimposed in the figure indicate the total capacitance values at which the energy curves reach their respective minima; these total capacitance values thus also indicate the optimal total capacitances for these particular capacitor configurations (i.e., 60, 120, and 172.2 μF for the one-capacitor, two-capacitor, and three-capacitor configurations, respectively, at the specific values of $\tau_m$ and $R_s$). As the graph further illustrates, while the optimal total capacitance of the three-capacitor configuration is greater than either of the simpler configurations, the relative stored energy it requires to reach threshold is significantly less than that needed for either one-capacitor or two-capacitor configurations across all values of total capacitance. For any fixed total capacitance, the largest relative reduction in energy requirements occurs when moving from the one-capacitor to two-capacitor configurations, although additional marginal energy savings are indeed realized by moving to the three-capacitor configuration. Table VI summarizes and compares these results for the selected set of data points associated with the drop-arrows on FIG. 28 (all stored energies are normalized by the minimum value from the three-capacitor configuration):

TABLE VI

| | Relative Stored Energy to reach $V_{th}$ | | | | | |
|---|---|---|---|---|---|---|
| $C_{total}$ | one-capacitor | two-capacitor | three-capacitor | 2 vs 1 | 3 vs 1 | 3 vs 2 |
| 60 | 1.411 | 1.150 | 1.107 | −18.5% | −21.6% | −3.7% |
| 120 | 1.527 | 1.087 | 1.012 | −28.8% | −33.8% | −7.0% |
| 172.2 | 1.692 | 1.104 | 1.000 | −34.8% | −40.9% | −9.4% |

Another important observation to be made from FIG. 28 is that the energy profile from the three-capacitor configuration is significantly "flatter" as a function of total capacitance than that from either of the other configurations, indicating that the three-capacitor configuration is likely to be more robust to variations or drift in underlying parameters or operating conditions.

Figure 29:
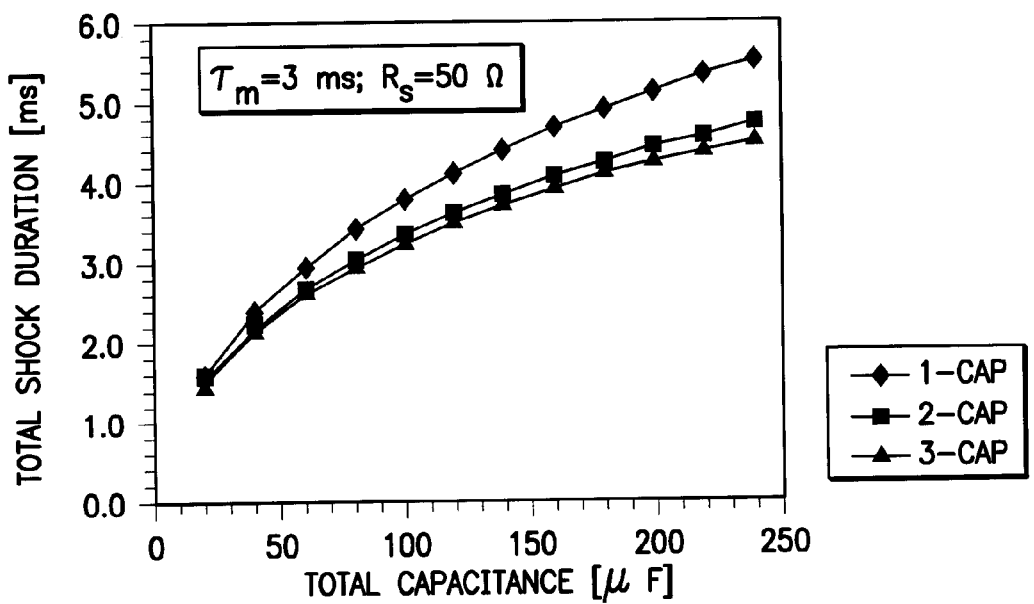
FIG. 29 is a graph the total duration needed to reach the myocardial defibrillation threshold as a function of total capacitance for one-, two- and three-capacitor shocking circuits showing that the total time required is less for the three-capacitor shocking circuit for all values of total capacitance.

Beyond a reduction in required stored energy, another advantage realized by using a three-capacitor configuration is that the total shock duration necessary to reach myocardial threshold is likewise shorter than that required by a one-capacitor or two-capacitor configuration. FIG. 29 illustrates this comparative advantage between the three-capacitor and one- and two-capacitor configurations based on the same system conditions used in FIG. 28. As expected, for all configurations, total shock duration is a monotonically increasing function of total system capacitance. However, the multi-step configurations are consistently shorter in duration than the simpler configurations. And, as with the relationship observed for total stored energy, for any fixed total capacitance, the largest relative reduction in total duration occurs when moving from the one-capacitor to two-capacitor configurations, although additional marginal duration shortening is indeed realized by moving to the three-capacitor configuration.

Table VII summarizes and compares these duration results for the selected set of data points:

TABLE VII

| | Total Duration (ms) to reach $V_{th}$ | | | | | |
|---|---|---|---|---|---|---|
| $C_{total}$ | one-capacitor | two-capacitor | three-capacitor | 2 vs 1 | 3 vs 1 | 3 vs 2 |
| 60 | 3.00 | 2.69 | 2.64 | −10.23% | −12.14% | −2.13% |
| 120 | 4.16 | 3.65 | 3.54 | −12.26% | −14.86% | −2.97% |
| 172.2 | 5.73 | 5.01 | 4.86 | −12.46% | −15.15% | −3.08% |

Exemplary ICD Design

Figure 30:
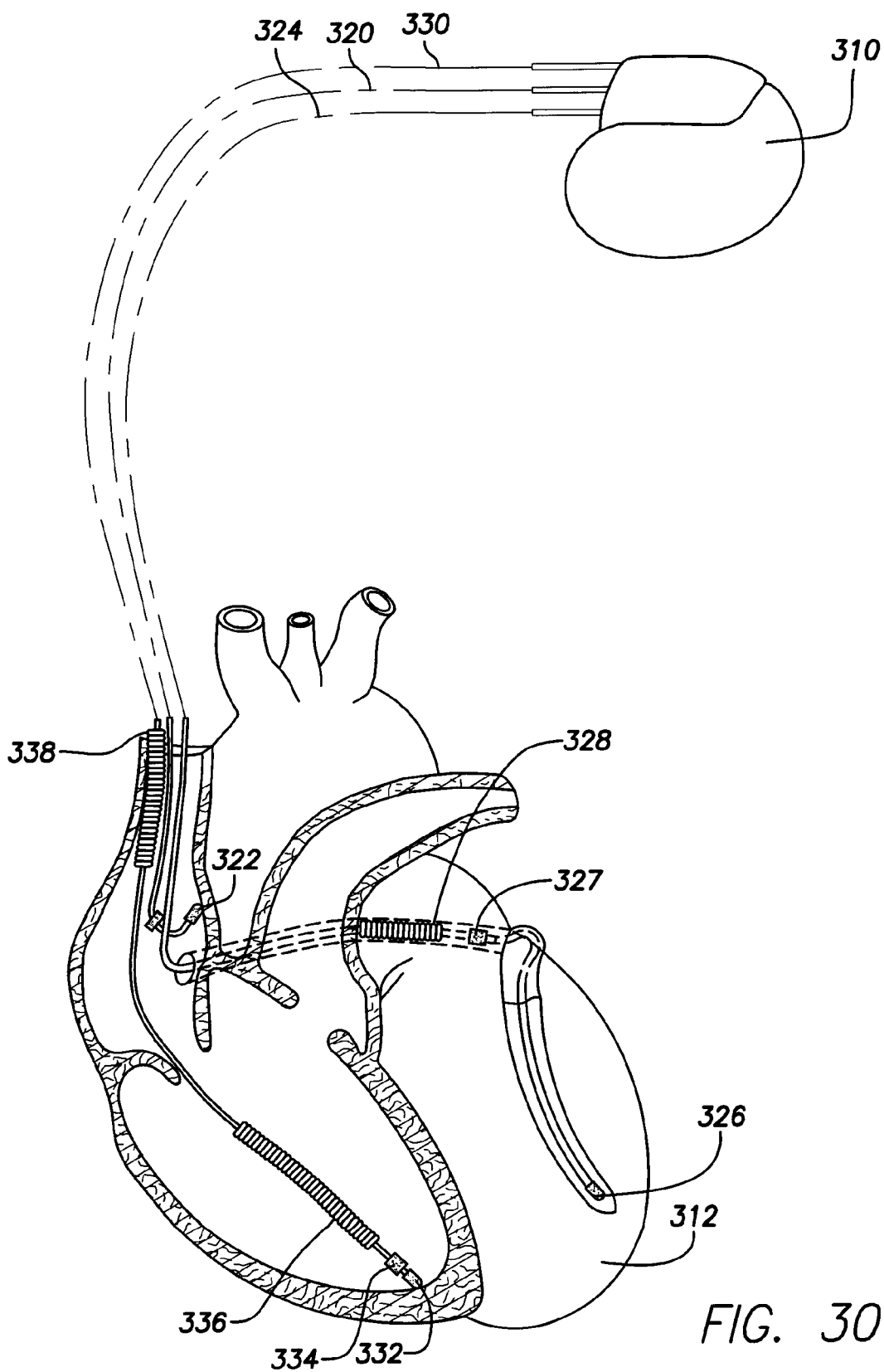
FIG. 30 is a simplified diagram illustrating an implantable stimulation device in electrical communication with at least three leads implanted into a patient's heart for delivering shock therapy in accordance with any of the shocking pulse waveforms described herein.

The invention may be implemented in an ICD configured as follows. As shown in FIG. 30, there is a stimulation device 310 in electrical communication with a patient's heart 312 by way of three leads, 320, 324 and 330, suitable for delivering multi-chamber stimulation and shock therapy. To sense a trial cardiac signals and to provide right a trial chamber stimulation therapy, the stimulation device 310 is coupled to an implantable right a trial lead 320 having at least an a trial tip electrode 322, which typically is implanted in the patient's right a trial appendage.

To sense left a trial and ventricular cardiac signals and to provide left chamber pacing therapy, the stimulation device 310 is coupled to a "coronary sinus" lead 324 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 324 is designed to receive a trial and ventricular cardiac signals and to deliver left ventricular pacing therapy using at least a left ventricular tip electrode 326, left a trial pacing therapy using at least a left a trial ring electrode 327, and shocking therapy using at least a left a trial coil electrode 328. For a complete description of a coronary sinus lead, and U.S. Pat. No. 5,466,254, "Coronary Sinus Lead with A trial Sensing Capability" (Helland), which patents are hereby incorporated herein by reference.

The stimulation device 310 is also shown in electrical communication with the patient's heart 312 by way of an implantable right ventricular lead 330 having, in this embodiment, a right ventricular tip electrode 332, a right ventricular ring electrode 334, a right ventricular (RV) coil electrode 336, and an SVC coil electrode 338. Typically, the right ventricular lead 330 is transvenously inserted into the heart 312 so as to place the right ventricular tip electrode 332 in the right ventricular apex so that the RV coil electrode will be positioned in the right ventricle and the SVC coil electrode 338 will be positioned in the superior vena cava. Accordingly, the right ventricular lead 330 is capable of receiving cardiac signals, and delivering stimulation in the form of pacing and shock therapy to the right ventricle.

Figure 31:
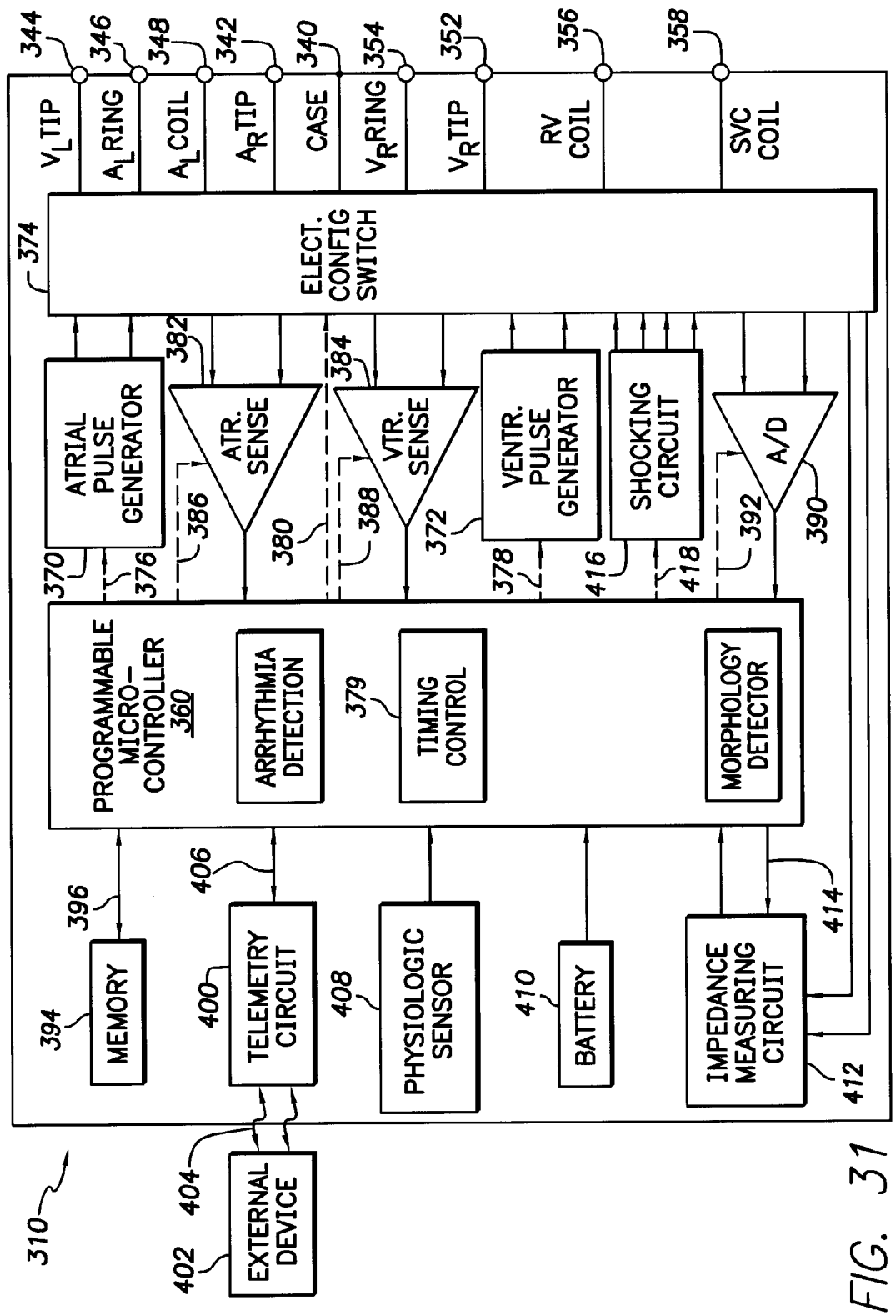
FIG. 31 is a functional block diagram of the multi-chamber implantable stimulation device of FIG. 30 illustrating the basic elements of a stimulation device that can provide cardioversion, defibrillation and pacing stimulation in four chambers of the heart.

As illustrated in FIG. 31, a simplified block diagram is shown of the multi-chamber implantable stimulation device 310, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 340 for the stimulation device 310, shown schematically in FIG. 30, is often referred to as the "can", "case" or "case electrode" and may be programmably selected to act as the return electrode for all "unipolar" modes. The housing 340 may further be used as a return electrode alone or in combination with one or more of the coil electrodes, 328, 36 and 38, for shocking purposes. The housing 340 further includes a connector (not shown) having a plurality of terminals, 342, 344, 346, 348, 352, 354, 356, and 358 (shown schematically and, for convenience, the names of the electrodes to which they are connected are shown next to the terminals). As such, to achieve right a trial sensing and pacing, the connector includes at least a right a trial tip terminal ($A_R$ TIP) 342 adapted for connection to the a trial tip electrode 322.

To achieve left chamber sensing, pacing and shocking, the connector includes at least a left ventricular tip terminal ($V_L$ TIP) 344, a left a trial ring terminal ($A_L$ RING) 346, and a left a trial shocking terminal ($A_L$ COIL) 348, which are adapted for connection to the left ventricular ring electrode 326, the left a trial tip electrode 327, and the left a trial coil electrode 328, respectively.

To support right chamber sensing, pacing and shocking, the connector further includes a right ventricular tip terminal ($V_R$ TIP) 352, a right ventricular ring terminal ($V_R$ RING) 354, a right ventricular shocking terminal ($R_V$ COIL) 356, and an SVC shocking terminal (SVC COIL) 358, which are adapted for connection to the right ventricular tip electrode 32, right ventricular ring electrode 334, the RV coil electrode 336, and the SVC coil electrode 338, respectively.

At the core of the stimulation device 310 is a programmable microcontroller 360 that controls the various modes of stimulation therapy. As is well known in the art, the microcontroller 360 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the present invention. Rather, any suitable microcontroller 360 may be used that carries out the functions described herein. The use of microprocessor-based control circuits for performing timing and data analysis functions are well known in the art.

As shown in FIG. 31, an a trial pulse generator 370 and a ventricular pulse generator 372 generate pacing stimulation pulses for delivery by the right a trial lead 320, the right ventricular lead 330, and/or the coronary sinus lead 324 via an electrode configuration switch 374. It is understood that in order to provide stimulation therapy in each of the four chambers of the heart, the a trial and ventricular pulse generators, 370 and 372, may include dedicated, independent pulse generators, multiplexed pulse generators, or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry 379 which is used to control the timing of such stimulation pulses (e.g., pacing rate, atrio-ventricular (AV) delay, a trial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

A trial sensing circuits 382 and ventricular sensing circuits 384 may also be selectively coupled to the right a trial lead 320, coronary sinus lead 324, and the right ventricular lead 330, through the switch 374 for detecting the presence of cardiac activity in each of the four chambers of the heart. Accordingly, the a trial (ATR. SENSE) and ventricular (VTR. SENSE) sensing circuits, 382 and 384, may include dedicated sense amplifiers, multiplexed amplifiers, or shared amplifiers. The switch 374 determines the "sensing polarity" of the cardiac signal by selectively closing the appropriate switches, as is also known in the art. In this way, the clinician may program the sensing polarity independent of the stimulation polarity.

Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables the device 310 to deal effectively with the difficult problem of sensing the low amplitude signal characteristics of a trial or ventricular fibrillation. The outputs of the a trial and ventricular sensing circuits, 382 and 384, are connected to the microcontroller 360 which, in turn, are able to trigger or inhibit the a trial and ventricular pulse generators, 370 and 372, respectively, in a demand fashion in response to the absence or presence of cardiac activity in the appropriate chambers of the heart.

For arrhythmia detection, the device 310 utilizes the a trial and ventricular sensing circuits, 382 and 384, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 360 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (AID) data acquisition system 390. The data acquisition system 390 is configured to acquire intra-cardiac electrogram signals, convert the raw analog data into a digital signal, and store the digital signals for later processing and/or telemetric transmission to an external device 402. The data acquisition system 390 is coupled to the right a trial lead 320, the coronary sinus lead 324, and the right ventricular lead 330 through the switch 374 to sample cardiac signals across any pair of desired electrodes.

The microcontroller 360 is further coupled to a memory 394 by a suitable data/address bus 396, wherein the programmable operating parameters used by the microcontroller 360 are stored and modified, as required, in order to customize the operation of the stimulation device 310 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 312 within each respective tier of therapy.

Advantageously, the operating parameters of the implantable device 310 may be non-invasively programmed into the memory 394 through a telemetry circuit 400 in telemetric communication with the external device 402, such as a programmer, transtelephonic transceiver, or a diagnostic system analyzer. The telemetry circuit 400 is activated by the microcontroller by a control signal 406. The telemetry circuit 400 advantageously allows intracardiac electrograms and status information relating to the operation of the device 310 (as contained in the microcontroller 360 or memory 394) to be sent to the external device 402 through an established communication link 404.

In the preferred embodiment, the stimulation device 310 further includes a physiologic sensor 408, commonly referred to as a "rate- responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states). Accordingly, the microcontroller 360 responds by adjusting the various pacing parameters (such as rate, AV Delay, V-V Delay, etc.) at which the a trial and ventricular pulse generators, 370 and 372, generate stimulation pulses.

The stimulation device additionally includes a battery 410 that provides operating power to all of the circuits shown in FIG. 31. For the stimulation device 310, which employs shocking therapy, the battery 410 must be capable of operating at low current drains for long periods of time, and then be capable of providing high-current pulses (for capacitor charging) when the patient requires a shock pulse. The battery 410 must also have a predictable discharge characteristic so that elective replacement time can be detected. Accordingly, the device 310 preferably employs lithium/silver vanadium oxide batteries, as is true for most (if not all) current devices.

As further shown in FIG. 31, the device 310 is shown as having an impedance measuring circuit 412 which is enabled by the microcontroller 360 via a control signal 414. The impedance measuring circuit 412 is not critical to the present invention and is shown for only completeness.

Since stimulation device 310 is intended to operate as an ICD, it must detect the occurrence of an arrhythmia, and automatically apply an appropriate electrical shock therapy to the heart aimed at terminating the detected arrhythmia. To this end, the microcontroller 360 further controls a shocking circuit 416 by way of a control signal 418. The shocking circuit 416 generates shocking pulses under the control of the microcontroller 360 using the techniques described above. The shocking circuit is configured as shown in FIG. 4 and may be programmed to generate any of the shocking pulse waveforms described above. The shocking pulses are applied to the patient's heart 312 through at least two shocking electrodes, and as shown in this embodiment, selected from the left a trial coil electrode 328, the RV coil electrode 336, and/or the SVC coil electrode 38. As noted above, the housing 340 may act as an active electrode in combination with the RV electrode 336, or as part of a split electrical vector using the SVC coil electrode 338 or the left a trial coil electrode 328 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level, delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Low Pain Pulse Generation

Figure 32:
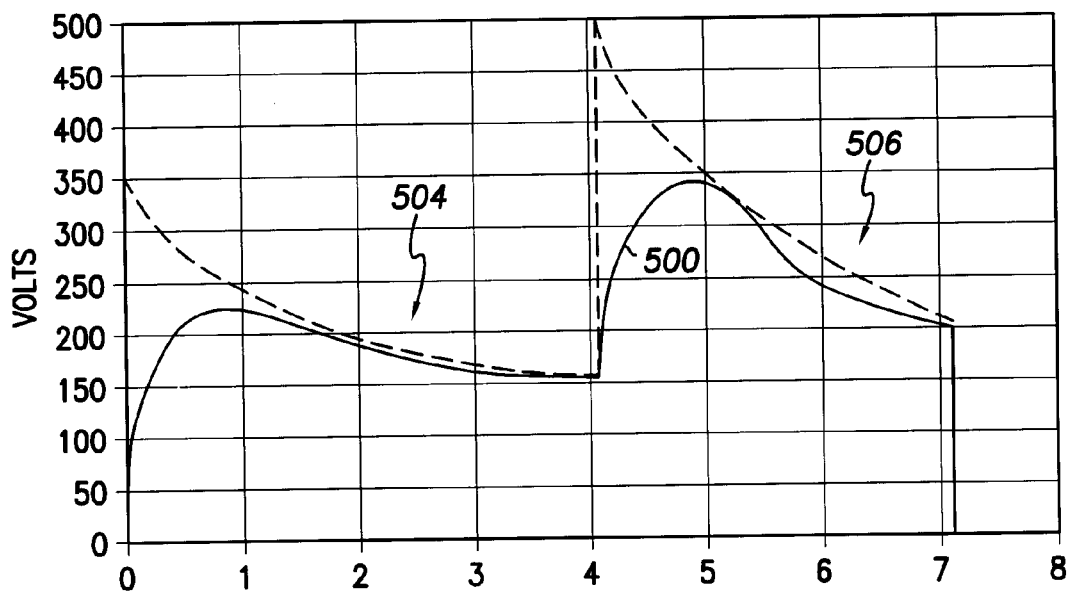
FIG. 32 illustrates a first exemplary low pain multi-step defibrillation waveform with rounded voltage peaks.
Figure 33:
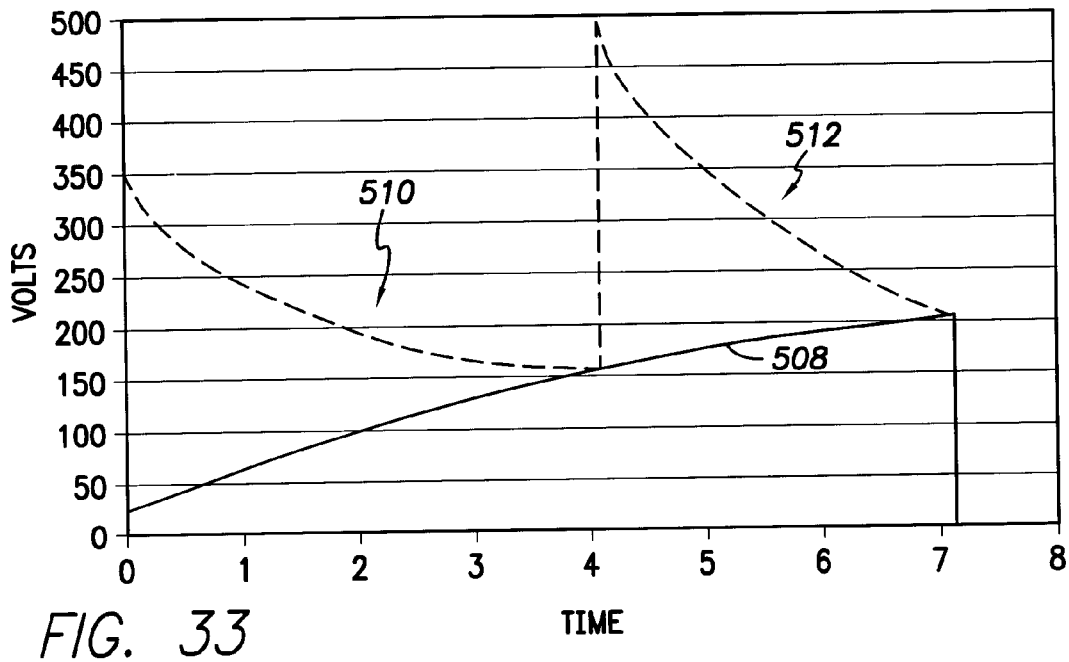
FIG. 33 illustrates a second exemplary low pain defibrillation waveform having significantly reduced voltage peaks.

FIG. 32 illustrates the positive phase of an exemplary low pain two-step defibrillation pulse 500, which includes a generally rounded first step or segment 504 followed by a generally rounded second step or segment 506, each having a rounded voltage peak. The voltage peaks are rounded to reduce the maximum voltage of each step to thereby reduce patient pain while still generating a sufficiently high final myocardial potential for reliable defibrillation. A non-rounded waveform generated by a two-capacitor system is shown in phantom lines in FIG. 32 to help illustrate the extent to which the peak voltage of each step is reduced from the two capacitor systems described above. FIG. 33 illustrates the positive phase of a rounded waveform 508 having even more significantly reduced voltage peaks to achieve even greater pain reduction. Waveform 508 is formed of a first rounded step or segment 510 and a second rounded step or segment 512 generated so as to form a single monotonically rising waveform. As can be seen from the phantom lines in FIG. 33, the initial voltage peaks of the equivalent non-rounded waveform are almost completely eliminated to thereby achieve substantial pain reduction.

Studies have shown that the pain associated with defibrillation or cardioversion shocks is largely due to the peak voltage associated therewith rather than due to the total amount of energy delivered to the patient. See, for example, "Testing Different Biphasic Waveforms and Capacitances: Effect on A trial Defibrillation Threshold and Pain Perception", Tomassoni et al., JACC Vol. 28, No. 3 September 1996:695–9 and "Pain Threshold for Low Energy Intracardiac Cardioversion of A trial Fibrillation with Low or No Sedation", Ammer et al., PACE Vol. 20, January 1997, Part II:230–236. Another study has suggested that the use of a rounded waveform can reduce to energy requirements of a cardioversion pulse and thereby possibly reduce the pain associated therewith. See "Rounded Biphasic Waveforms Reduces Energy Requirements for Transvenous Catheter Cardioversion of a trial Fibrillation and Flutter", Harbinson et al., PACE Vol. 20 January 1997, Part II:226–9. More specifically, the Harbinson article illustrates a biphasic waveform having a rounded leading edge rising to a peak voltage followed by a linearly decreasing, truncated waveform.

Although the waveform of the Harbinson article is likely to be effective for use in reducing pain in the patient, the shape of the waveform cannot be easily generated using relatively simple RC defibrillation circuitry and hence may not be practical or use within ICDs. In this regard, generation of the waveform described in the Harbinson article would likely require a full RLC circuit. RLC circuits are not typically used in defibrillation circuits of ICDs due to power and size constraints.

Figure 34:
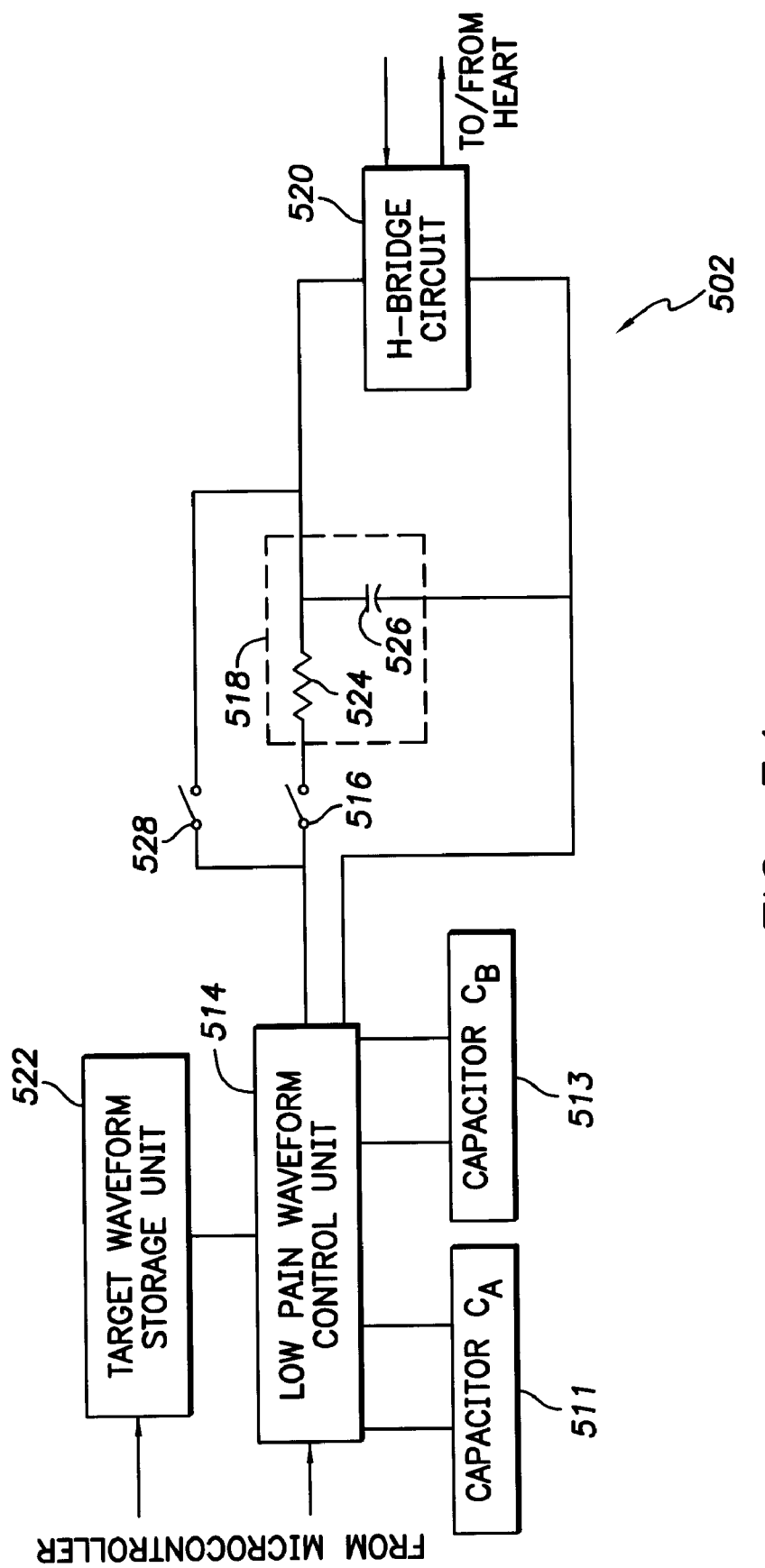
FIG. 34 is a simplified schematic diagram of a two-capacitor ICD RC shocking circuit configured in accordance with an embodiment of the invention for generating low pain waveforms that approximate the waveforms of FIGS. 32 and 33.

FIG. 34 illustrates a defibrillation shocking circuit 502 that generates generally rounded waveform shapes for achieving pain reduction, yet requires no RLC circuitry. Without inductors, RC shocking circuit 502 can only approximate the idealized rounded waveform shapes of FIGS. 32 and 33. Yet by approximating the idealized rounded shapes, the RC circuit nevertheless achieves significant pain reduction.

RC shocking circuit 502 includes first and second shocking capacitors 511 and 513 coupled to a low pain waveform control unit 514 which includes parallel/series switching components of the type described above with reference to FIG. 3 for alternately discharging the two capacitors either in parallel or in series. Output lines of the control unit are coupled through a chopping switch 516 and an RC filter 518 to an H-bridge output circuit 520, which in turn is coupled to patient heart tissue for delivering a shock to the heart tissue. RC filter 518 includes a filter resistor 524 and a filter capacitor 526.

In use, the chopping switch is toggled at a high switching rate by the control unit so that voltage applied to the H-bridge through the RC-filter increases briefly while the chopping switch is closed and decreases briefly while the switch is open to minimize significant voltage swings in the resulting defibrillation pulse. A bypass switch 528 is provided to bypass the chopping switch and the RC-filter to generate a non-rounded pulse if needed. Thus, if a rounded pulse fails to properly defibrillate the heart, one or more conventional non-rounded shocking pulses can then be generated in an effort to ensure proper defibrillation. The shocking capacitors, the chopping circuit, the bypass and the H-bridge are all controlled by low pain control unit 514 so as to produce an output waveform approximating a target rounded waveform shape stored in an target waveform storage unit 522. In FIG. 34, for clarity in illustrating the overall circuit, control unit 514 is shown only in block diagram form and various control line interconnections to the other components, such as to the chopping switch, are not specifically shown.

To approximate the monotonically-rising shocking pulse of FIG. 33, shocking circuit 502 is configured with the circuit parameters of Table VIII.

TABLE VIII

| $C_A$ and $C_B$ (each) | 200 uF | Estimated Initial Energy in Capacitors | 32 Joules |
|---|---|---|---|
| Load | 50 ohm | $V_{starting}$ | 400.0 volts |
| C filter | 5 uF | $V_{peak}$ | 200 volts |
| R filter | 10 ohm | $V_{initial}$ | 25 volts |
| R thevenin | 8.33 ohm | Switch delay | 10 us |
| Volt. Divider fraction | 0.83 | | |
| shock τ | 6 ms | | |

In the Table VIII, $V_{starting}$ represents the starting voltage applied across the RC filter, $V_{initial}$ represents the initial voltage of the first step of the target waveform being approximated, and $V_{peak}$ represents the peak voltage of the target waveform. The switch delay represents the period of time that the chopping switch is held open whenever the voltage of the output waveform exceeds the target waveform voltage. $R_{thevenin}$ represents the effective resistance of circuit components connected to the input of the chopping switch. The voltage divider fraction represents the extent to which voltage input to the RC filter is reduced by the RC filter. The estimated initial energy represents the amount of energy stored in the capacitors prior to delivery of the pulse. Not all energy from the capacitors is delivered to the patient. Energy is lost during generation of the pulse as a result of the techniques employed to round the pulse to reduce pain. However, as will be further explained below, by using a two capacitor system (that can be switched from parallel to series while the pulse is being generated) considerably less energy is lost than in a similar system employing a single shocking capacitor.

With the parameters of TABLE VII, the circuit approximates a rounded pulse waveform that increases sharply from zero volts to about 25 volts, then rises generally exponentially up to a rounded peak of 200 volts, then decreases sharply back toward zero volts. The central exponential portion approximates an exponential shape approximated by:

$$V_{waveform}=V_{initial}+(V_{peak}-V_{initial})*(1-e^{-t/T}). \qquad (\text{Eq. 58})$$

The positive phase of an exemplary resulting pulse waveform generated by shocking circuit 502 using the parameters of TABLE VIII is shown in FIG. 35, which includes a graph 550 of the output shock voltage as a function of time (in ms) and a graph 552 of the voltage across the capacitors. As can be seen, the waveform generated by the shocking circuit closely approximates the target waveform shape shown in FIG. 33 and is believed to be effective in reducing patient pain since the waveform has no sharp voltage peaks. Note also, the sharp increase in voltage across the capacitors caused by switching the capacitors from parallel to series following point 554. In FIG. 35, data points are shown as being interconnected by straight lines. In actuality, the voltage does not typically change linearly between each point, but exponentially. The straight lines in the figure are provided to help illustrate the general trend of the voltage and are not intended to represent the actual voltage at each point in time. Also, in FIG. 35, the voltage graphs shown therein end at a point 556 when the shocking capacitors are disconnected from the chopping circuit and hence do not show the output waveform voltage returning to zero. Nor does the figure show the subsequent negative phase of the pulse, which may have a modest negative voltage spike followed by an exponentially voltage decay back to zero volts.

Figure 36A:
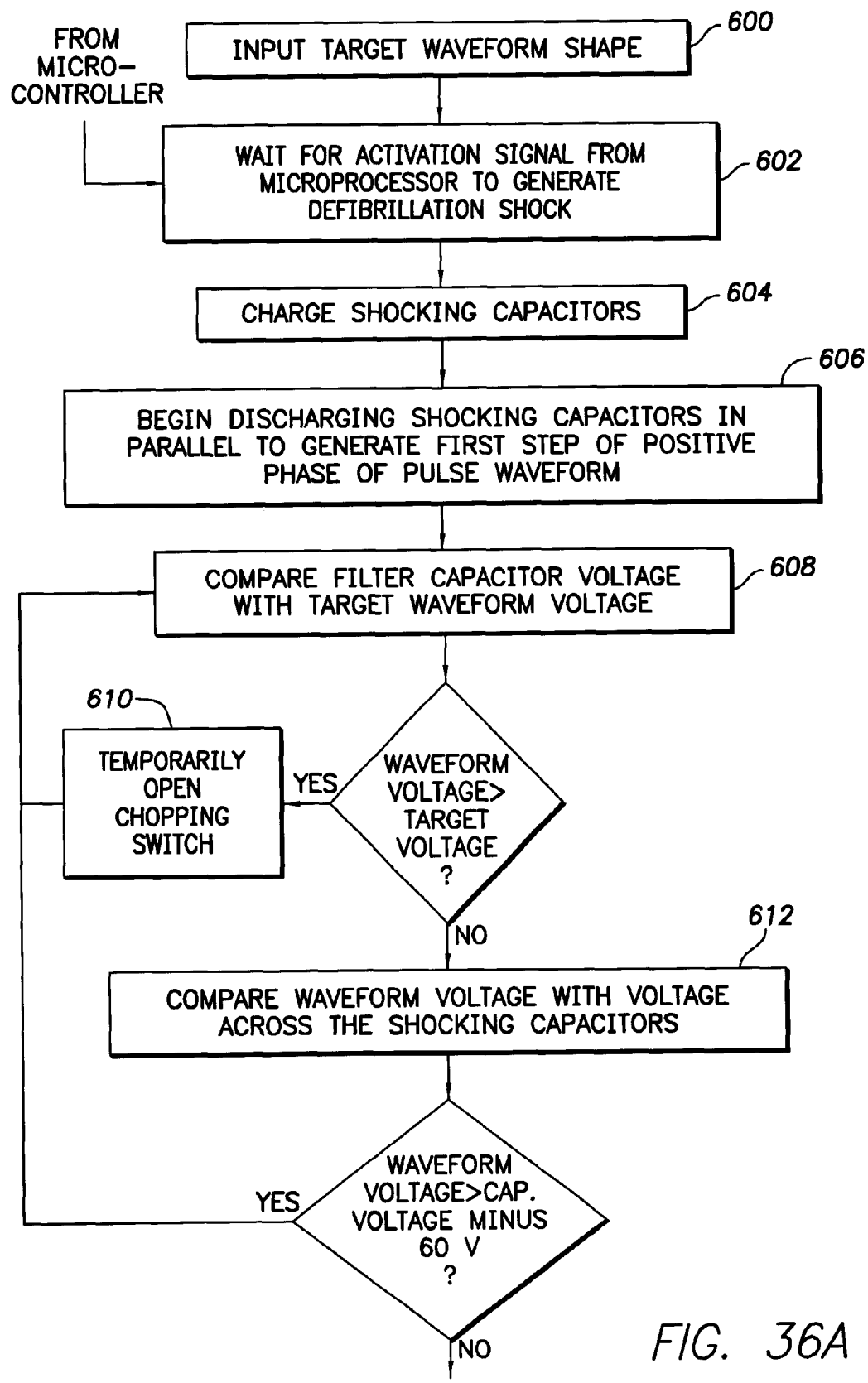
FIGS. 36A and 36B depict a flow chart providing illustrating a method for generating the low pain defibrillation waveform of FIG. 35 using the circuit of FIG. 33.
Figure 36B:
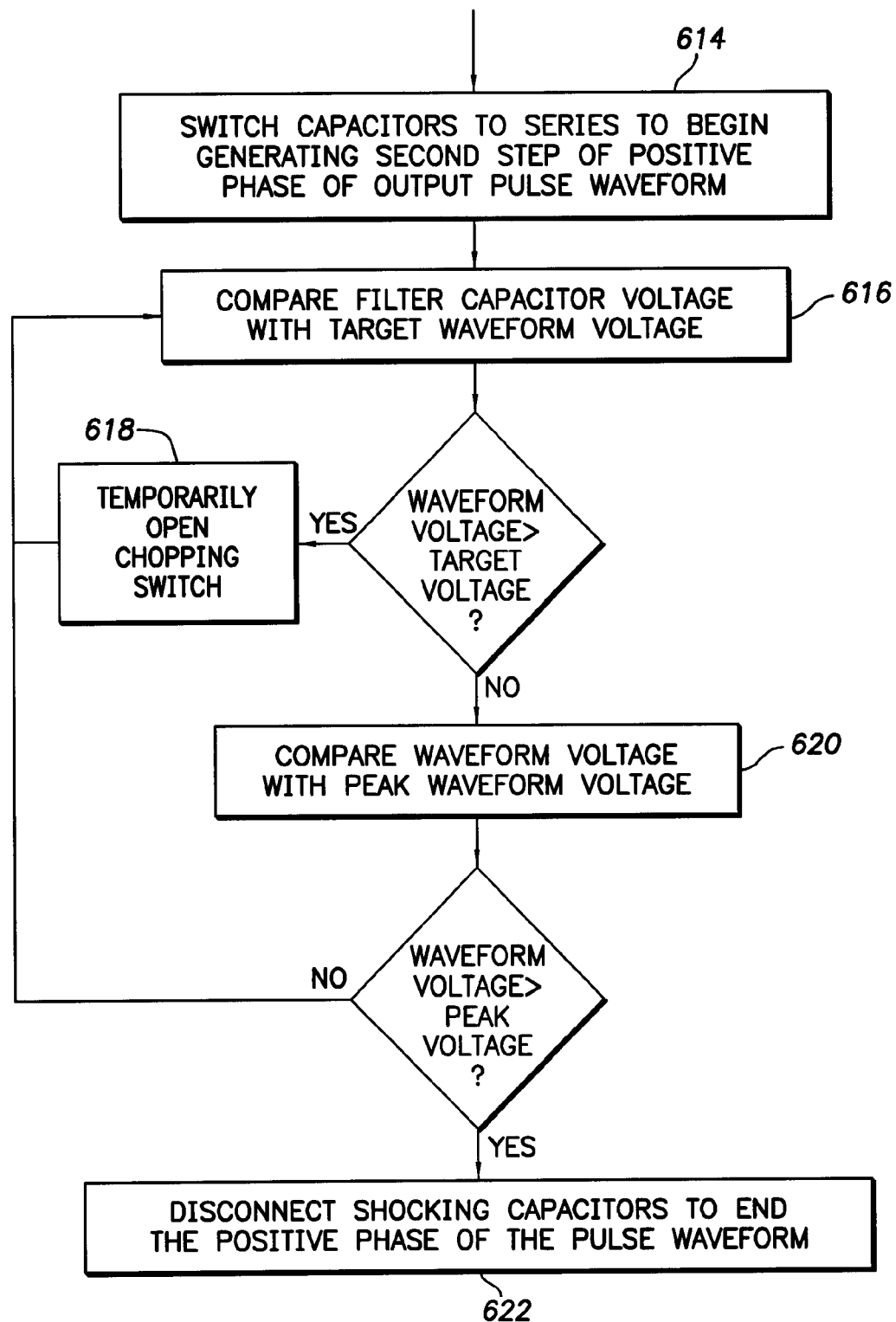

The method of operating the two-capacitor circuit of FIG. 34 is set forth in FIGS. 36A and 36B. Initially, at step 600, the rounded target waveform shape to be approximated is input digitally into control circuit 514 from the microcontroller of the ICD. As one example, a digitized version of the rounded shape (508) of FIG. 33 is input and stored. The stored digitized shape is then converted to analog via a digital to analog converter within the control unit to permit ease of comparison with various analog circuit voltages detected by the control unit. At step 602, the circuit awaits an activation signal from the microcontroller instructing it to deliver a shocking pulse. Once the signal is received, the control circuit charges capacitors $C_A$ and $C_B$ to $V_{starting}$ at step 604 and then begins discharging the capacitors in parallel at step 606 (at an effective capacitance of 400 mF) to begin generating the first step of the positive phase of the pulse waveform.

While the capacitors are being discharged in parallel, the control circuit at step 608 monitors the voltage across the filter capacitor and compares it to the voltage of the target waveform being approximated. Whenever the filter capacitor voltage exceeds the target waveform voltage, the control circuit opens the chopping switch for 10 ms at step 610 to thereby slightly decrease the filter capacitor voltage and then closes the chopping switch to permit the filter capacitor voltage to rise again. In this manner, the actual waveform voltage approximately tracks the target waveform voltage. At step 612, the control circuit compares the voltage across capacitors $C_A$ and $C_B$ to the output voltage of the shocking pulse and, so long as the capacitor voltage remains more than 60 V (or some other predetermined voltage value) above the waveform voltage, execution loops back to step 608 for continued generation of the first step of the waveform. As the first step of the pulse is generated, the voltage across the capacitors drops from the starting voltage (400V) and the waveform voltage increases from 0V. When the capacitor voltage drops to only 60 V above the waveform voltage (point 554 of FIG. 35), the control circuit switches the capacitors to series at step 614 causing the voltage across the capacitors to increase sharply so that the shocking circuit can thereby begin to generate the second step of the two-step pulse.

While the capacitors are being discharged in series, the control circuit compares the voltage across the filter capacitor to the target voltage, at step 616, and opens the chopping switch temporarily at step 618 whenever the filter capacitor voltage exceeds the target waveform voltage so as to continue to track the target waveform voltage. The control circuit also compares the waveform voltage to the peak voltage ($V_{peak}$) at step 620 and, as soon as the waveform voltage exceeds the peak voltage (at point 556 of FIG. 35), the output waveform is truncated by disconnecting the capacitors from the RC filter at step 622 thereby permitting the output waveform voltage to drop back to zero and hence terminating the second step of the two-step positive phase of the pulse waveform. Alternatively, the output waveform is truncated after a preprogrammed period of time.

Thus FIGS. 36A and 36B set forth a method for providing a defibrillation waveform pulse that approximately tracks an input target waveform shape. Although described with respect to approximating the waveform shape of FIG. 33 that rises smoothly and monotonically to a peak voltage then immediately drops to zero, the technique of FIGS. 36A and 36B can be used to approximate a wide variety of other waveform shapes, such as the waveform shown in FIG. 32. The monotonically rising shape of FIG. 33 is preferred as is believed it provides for greater pain reduction. Also, although the chopping technique of FIGS. 36A and 36B utilizes the two-capacitor circuit of FIG. 34, the technique can be exploited using other circuits as well such as single capacitor circuits or circuits having three or more shocking capacitors. Hence, the circuit of FIG. 34 and the method of FIGS. 36A and 36B are merely examples of the general techniques of the invention. Note that the values shown TABLE VIII are also merely exemplary. Other exemplary values for the various circuit and waveform parameters are: $C_A$ and $C_B$ in the range of 100 to 300 $\mu$F each, load in the range of 25 to 100 ohms, C filter in the range of 1–25 $\mu$F, R filter in the range of 0 to 20 ohms, 96 in the range of 0.1 to 20 ms, $V_{starting}$ in the range of 20 to 600 volts, $V_{peak}$ in the range of 40 to 600 V, $V_{initial}$ may be in the range of 0 to 200 Volts, and the switch delay in the range of 5 to 20 ms.

By configuring and operating the shocking circuit as just summarized, the waveform is rounded to eliminate voltage peaks so as to reduce patient pain while losing considerably less energy than would occur with a similar single capacitor system. Referring again to FIGS. 32 and 33, phantom lines provided therein represent a two-step waveform that would be generated by the two-capacitor system if the waveform rounding techniques of the invention were not employed. The total surface area under the phantom lines represents the total amount of energy required to generate the pulse waveform. The surface area under the rounded pulse waveform represents the energy of the pulse itself. Hence the difference in energy represents the amount of energy that is lost to achieve the rounded pulse shape to reduce patient pain. This energy is primarily lost as heat in the various resistors of the shocking circuit.

Although some energy is lost using the two capacitor system, the amount of energy lost is considerably less than if a single capacitor system were instead employed to generate the same rounded pulse using the same chopping technique. The single capacitor system would need to be capable of achieving a much higher starting voltage ($V_{starting}$) than the two-capacitor system in order to generate the same rounded waveform. In FIG. 32, for example, the starting voltage would have to be sufficiently high so that, even after the voltage decayed exponentially for 5 ms, the voltage would still be nearly 350 V to permit generation of the second step of the pulse. In FIG. 33, for example, the starting voltage would have to be sufficiently high so that, even after the voltage exponentially decays for 7 ms, the voltage would still be over 200 V to permit generation of the final peak of the of the pulse. Moreover, to achieve the much higher starting voltage, the single capacitor would need to be physically much larger and heavier than the two separate capacitors thereby increasing the size, weight and cost of the ICD.

Hence, the use of a two capacitor multi-step shocking system in combination with waveform rounding techniques achieves reduced patient pain without significant penalties in terms of size, weight, cost and power consumption of the ICD. Depending upon the specific implementation, a still further reduction in overall size, weight, cost and power consumption can be achieved using an even greater number of shocking capacitors, such as three or four. The two-capacitor system is merely on example of a system that exploits the principles of the invention. Also, although greater penalties in terms of size, weight, cost and power consumption may occur with a single shocking capacitor system employing the RC circuit of the invention, pain reduction is still be achieved by virtue of rounding the shocking pulse and hence single capacitor systems exploiting the chopping technique of the invention are also useful.

While the invention herein disclosed has been described by means of specific embodiments and applications thereof, numerous modifications and variations could be made thereto by those skilled in the art without departing from the scope of the invention set forth in the claims.

What is claimed is:

1. In an implantable defibrillator for implantation within a patient, a method comprising:

generating a shocking waveform by approximating a selected waveform that continually increases in magnitude up to a peak voltage and that then decreases sharply; and applying the shocking waveform to heart tissue of the patient.

2. The method of claim 1, wherein the selected waveform being approximated comprises an initial portion that increases sharply from zero voltage to an initial voltage ($V_{initial}$), a central portion that increases exponentially from the initial voltage to the single peak voltage ($V_{peak}$), and a tail portion that decreases sharply back to zero voltage.

3. The method of claim 2, wherein the central portion comprises an input rounded waveform being approximated by an exponential shape represented by:

$$V_{waveform} = V_{initial} + (V_{peak} - V_{initial})*(1 - e^{-t/T}).$$

4. The method of claim 3, wherein $V_{initial}$ is in the range of 20–30 Volts, $V_{peak}$ is in the range to 250–350 Volts, and T is within the range of 5–7 milliseconds.

5. The method of claim 1 wherein the selected waveform is an input waveform and wherein generating the shocking waveform that approximates the input waveform comprises:

a) increasing a magnitude of the voltage of the shocking waveform as a function of time;

b) comparing the voltage of the shocking waveform to the input waveform as a function of time;

c) whenever the magnitude of the shocking waveform exceeds the magnitude of the input voltage, decreasing the magnitude of voltage of the shocking waveform until it again falls below the magnitude of input voltage; and d) repeating steps a)–c), such that the shocking waveform generally approximates the input waveform.

6. The method of claim 5 wherein steps a) through c) are repeated until the magnitude of the voltage of the shocking waveform exceeds the peak voltage, then performing the additional step of decreasing the magnitude of the voltage of the shocking waveform to zero.

7. The method of claim 1 for use in a defibrillator having a shocking circuit with a shocking capacitor, a resistive-capacitive (RC) filter, and a chopping switch interconnecting the shocking capacitor and the RC filter, wherein the selected waveform is an input waveform, and wherein generating the shocking waveform that approximates the input waveform comprises repeatedly opening and closing the chopping switch so as to produce an output from the RC filter that approximates the input waveform.

8. The method of claim 7 for use in a defibrillator also having a storage unit storing a representation of the input waveform and wherein repeatedly opening and closing the chopping switch so as to produce an output from the RC filter that approximates the input waveform comprises:

detecting a magnitude of the voltage output from the RC filter as a function of time;

comparing the magnitude of the voltage to the magnitude of the input waveform as a function of time; and opening the chopping switch for a predetermined period of time whenever the magnitude of the voltage output from the RC filter exceeds the magnitude of the input voltage and then closing the chopping switch, the predetermined period of time being sufficient to permit the magnitude of the voltage output from the RC filter to fall below the magnitude of the input voltage.

9. The method of claim 8 wherein the predetermined period of time is in the range of 5 to 7 ms.

10. The method of claim 1, wherein the selected waveform is an input waveform and wherein generating the shocking waveform comprises:

generating a first step of a multi-step shocking waveform, the first step of the shocking waveform approximating a first portion of the input waveform having a voltage magnitude that increases monotonically from zero volts to a voltage intermediate zero volts and the single peak voltage; and generating a second step of the multi-step shocking waveform, the second step of the shocking waveform approximating a second portion of the input waveform having a voltage magnitude that increases monotonically from the intermediate voltage to the single peak voltage.

11. The method of claim 10 for use in a defibrillator having a shocking circuit with first and second capacitors, a resistive-capacitive (RC) filter; and a low pain waveform control unit connected to the capacitors and operative to selectively discharge the capacitors through the RC filter to generate a rounded, multi-step defibrillation pulse waveform and wherein the first step of the multi-step shocking waveform is generated by discharging the first and second capacitors in parallel while periodically shunting a portion of charge through the RC filter to reduce a peak voltage of the first step of the pulse waveform; and wherein the second step of the multi-step shocking waveform is generated by periodically discharging the first and second capacitors in series while periodically shunting a portion of the charge through the RC filter to reduce a peak voltage of the second step of the pulse waveform.

12. In an implantable defibrillator for implantation within a patient, a shocking circuit comprising:

means for inputting a selected waveform shape that continually increases in magnitude up to a peak voltage and that then decreases sharply;

means for generating a shocking waveform that approximates the input waveform; and means for applying the shocking waveform to heart tissue of the patient.

13. The shocking circuit of claim 12 wherein the means for generating the shocking waveform that approximates the input waveform comprises:

means for increasing a magnitude of the voltage of the shocking waveform as a function of time;

means for comparing the voltage of the shocking waveform to the input waveform as a function of time;

means, operative whenever the magnitude of the shocking waveform exceeds the magnitude of the input voltage, for decreasing the magnitude of voltage of the shocking waveform until it again falls below the magnitude of input voltage.

14. The shocking circuit of claim 12, wherein the means for generating the waveform comprises:

means for generating a first step of a multi-step shocking waveform, the first step of the shocking waveform approximating a first portion of the input waveform having a voltage magnitude that increases monotonically from zero volts to a voltage intermediate zero volts and the single peak voltage; and means for generating a second step of the multi-step shocking waveform, the second step of the shocking waveform approximating a second portion of the input waveform having a voltage magnitude that increases monotonically from the intermediate voltage to the single peak voltage.

15. In a defibrillator, a shocking circuit comprising:

at least one capacitor;

a resistive-capacitive (RC) filter; and switching circuitry connected to the capacitors and operative to selectively discharge the capacitor through the RC filter to generate a first phase of a defibrillation pulse waveform by approximating an input waveform that continually increases in magnitude up to a peak voltage and that then decreases sharply.

16. The shocking circuit of claim 15 further comprising first and second capacitors, and wherein the switching circuitry comprises:

an output circuit connected to the RC filter;

a chopping switch coupled between the first and second capacitors and the RC filter; and a control unit that is operative to alternately couple the storage capacitors to the chopping switch either in parallel or in series and to control the chopping switch to periodically shunt current from the capacitors through the RC filter to the output circuit.

17. The shocking circuit of claim 16 wherein the output circuit is an H-bridge.

18. In an implantable defibrillator for implantation within a patient, a shocking circuit comprising:

an RC filter;

a chopping switch that is operative to selectively deliver energy to the RC filter;

an H-bridge output circuit connected to the output of the RC filter; and a control unit connected to the chopping switch, the control unit being operative to control the chopping switch to deliver energy to the RC filter, wherein the filter, switch and H-bridge output circuit cooperate to generate an output waveform that has a continually increasing energy level to a peak level and that then decreases rapidly.

* * * * *